United States Patent [19]

Chen et al.

[11] Patent Number: 5,547,876
[45] Date of Patent: Aug. 20, 1996

[54] COMBUSTION ACCELERATORS, PROCESSES FOR THEIR PRODUCTION AND PROCESSES FOR THEIR USE IN ELEMENTAL ANALYSIS

[75] Inventors: Ching-Fong Chen, Baroda; Carlos Guerra, Berrien Springs, both of Mich.

[73] Assignee: Leco Corporation, St. Joseph, Mich.

[21] Appl. No.: 313,018

[22] Filed: Sep. 27, 1994

[51] Int. Cl.⁶ .................................................. G01N 25/22
[52] U.S. Cl. .......................... 436/159; 436/119; 436/120; 436/121; 436/122; 436/123; 436/133; 436/155; 436/160; 436/181; 501/17; 501/32
[58] Field of Search ............................ 436/119–123, 133, 436/155, 159, 160, 181; 501/17, 32

[56] References Cited

U.S. PATENT DOCUMENTS

| | | | |
|---|---|---|---|
| 3,278,318 | 10/1966 | Hensler et al. | 106/47 |
| 3,642,583 | 2/1972 | Greenberg et al. | 588/201 |
| 4,041,217 | 8/1977 | Collins | 429/112 |
| 4,743,302 | 5/1988 | Dumesnil et al. | 106/1.23 |
| 4,833,105 | 5/1989 | Kurasawa | 501/44 |
| 5,204,270 | 4/1993 | LaCount | 436/159 X |
| 5,206,355 | 4/1993 | Richards et al. | 536/4.1 |
| 5,262,363 | 11/1993 | Yoshida et al. | 501/17 |
| 5,348,914 | 9/1994 | Thometzek et al. | 501/17 X |

FOREIGN PATENT DOCUMENTS 59-168352  9/1984  Japan.

OTHER PUBLICATIONS

H. Zenda et al. *Chem. Pharm. Bull.* 1979, 27, 1015–1020.
Z. Hu et al. *J. Catal.* 1989, 119, 33–46.
Y. Baba *Chem. Abstr.* 1990, 113, 128868h.
S. Imamura et al. *Nippon Kagaku Kaishi* 1991, 645–647.

*Primary Examiner*—Arlen Soderquist
*Attorney, Agent, or Firm*—Price, Heneveld, Cooper, DeWitt & Litton

[57] ABSTRACT

Non-toxic combustion decomposition accelerators and processes for their production for elemental analysis. The non-toxic accelerators may be either single component or multicomponent. The single component non-toxic accelerators are glass frit, niobium pentoxide, and inorganic phosphate compounds. The multicomponent accelerators are formed from a combination of the foregoing, and most preferably from (a) one or more of niobium pentoxide, tungsten oxide and mixtures thereof, and (b) one or more of glass frit, inorganic phosphate compounds, and mixtures thereof.

38 Claims, 29 Drawing Sheets

COMBUSTION ACCELERATORS, PROCESSES FOR THEIR PRODUCTION AND PROCESSES FOR THEIR USE IN ELEMENTAL ANALYSIS

BACKGROUND OF THE INVENTION

This invention relates to combustion accelerators for use in elemental combustion analysis, the compositions thereof and to processes for their production.

Elemental combustion analysis is important in many major industries, including food, pharmaceuticals, chemicals, plastics, coal, coke, ceramics, steel, etc. The total quantity of an element or elements in a material is most often used to justify quality of a product. In many cases the element determination must be accurate and performed on a timely basis in order to allow production control to make appropriate adjustments in processing and allow for a timely product delivery.

In many combustion analyzers the sample material is combusted in an oxygen environment to release the various forms of elements as oxides. However, different types of elements with different strength of bonding may exist in a material, each of which may dissociate at a varying rate, creating a low analyzed result or a very long analysis time.

A typical example is sulfur in various organic and inorganic compounds. To avoid the problems of a low analyzed result or a very long analysis time, vanadium pentoxide ($V_2O_5$) has traditionally been mixed with the sample to be analyzed, in order to accelerate sulfur release as $SO_2$. However, recent concern over the toxicity of vanadium pentoxide has created a need for a new, non-toxic "accelerator" which can be used for elemental composition analysis.

In cases where objections to the use of vanadium oxide ($V_2O_5$) exist, or no vanadium oxide ($V_2O_5$) is available, high purity tungsten oxide ($WO_3$) has been substituted for vanadium oxide ($V_2O_5$) as a combustion aid. See LECO Corporation Application Bulletin, Form No. 203-601-229, August, 1992. Like vanadium oxide ($V_2O_5$), tungsten oxide ($WO_3$) is useful for its ability to assist in elemental oxidation during the combustion analysis process. However, the results obtained by using tungsten oxide ($WO_3$) as the sole accelerator are not as beneficial as those obtained by vanadium oxide ($V_2O_5$).

SUMMARY OF THE INVENTION

In the present invention, glass frit, niobium pentoxide, and inorganic phosphates are used individually or in combination as combustion decomposition accelerators in the elemental analysis of substances. These have been discovered to be excellent non-toxic accelerators.

DESCRIPTION OF THE PREFERRED EMBODIMENT

Figure 1:
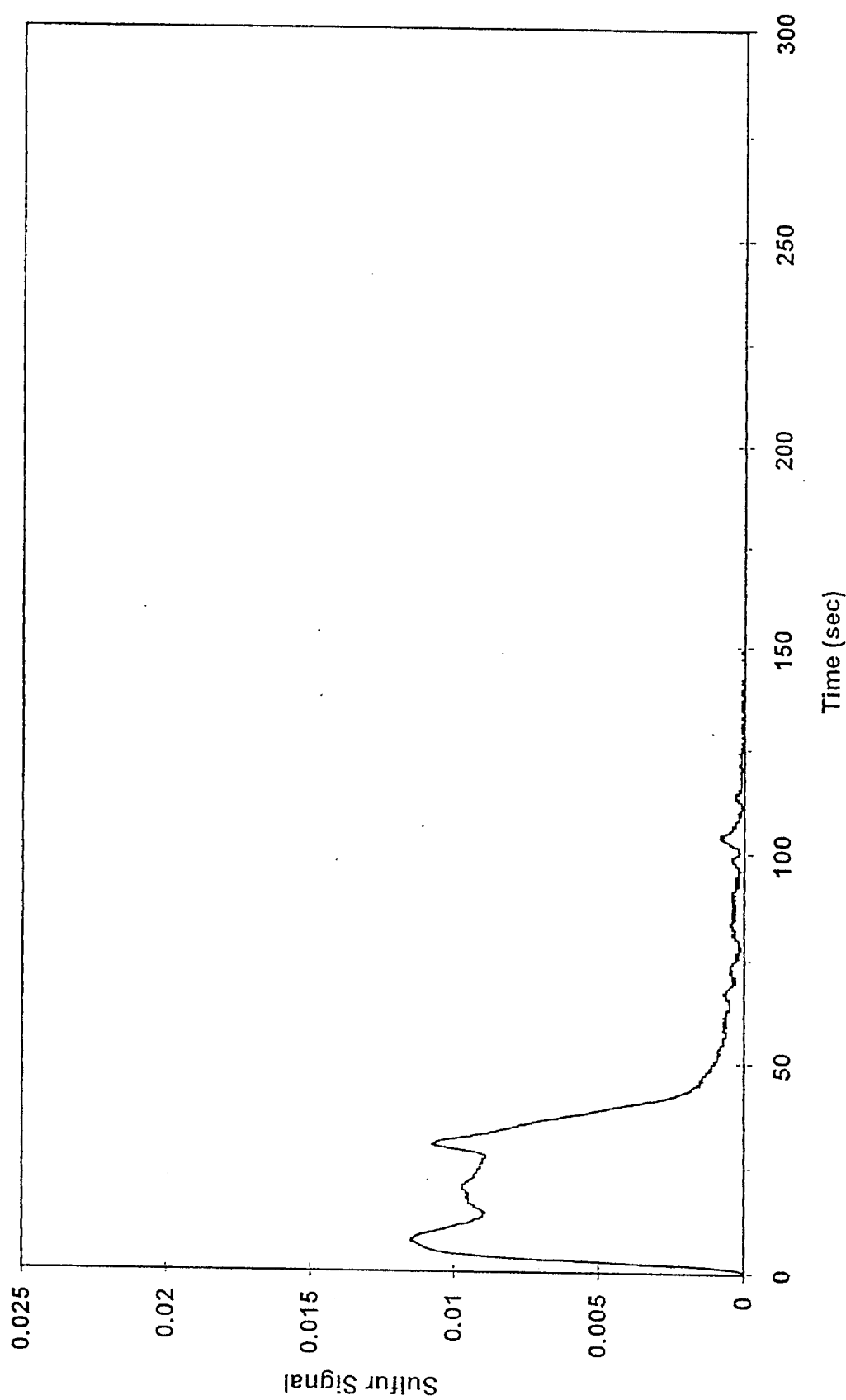
FIG. 1 shows the sulfur signal as a function of time for tobacco with Ferro 3249 glass frit as the accelerator.

In the preferred embodiment a non-toxic accelerator, comprising one or a mixture of glass frit, an inorganic phosphate compound, or niobium pentoxide ($Nb_2O_5$), is mixed with a substance to be analyzed in a ratio of from about two grams (2.0 gm) to about 0.15 grams accelerator to substance, and placed in a combustion container. This ratio is merely a preferred ratio; the ratio of accelerator to substance can vary within usual ranges used in the art. The container is placed in a combustion analyzer, and the mixture heated from about 450° C. to about 1450° C., depending on the substance to be analyzed and the specific test protocol used. The combustion gasses are analyzed for the desired elements. The accelerator may be a single component compound comprising glass frit, an inorganic phosphate compound, or niobium pentoxide, or the accelerator may be a multicomponent compound formed by mixing at least one of glass frit and/or an inorganic phosphate compound with niobium pentoxide ($Nb_2O_5$). The accelerator may include other ingredients, with some advantage being afforded by the addition of tungsten oxide ($WO_3$) to glass frit and/or an inorganic phosphate. In addition to being non-toxic, the accelerators of the preferred embodiment reduce the time required for elemental decomposition in an organic or inorganic compound to at least one half of the analysis time when no accelerator is used.

Preferably, the accelerator has a particle size of no more than about 2 mm, with the preferred particle size being from about 0.1 to about 20 µm. The only restriction on the amount of impurities is that the accelerator should not contain as a significant impurity the element being tested for.

The glass frit utilized can be a commercially available powder or a special formulated glass frit. Additionally, the glass frit can be either a leaded glass frit or a leadless glass frit.

A more preferred glass frit is Ferro 3249, which comprises less than about 5% by weight calcium oxide (CaO), from about 5% to about 15% by weight magnesium oxide (MgO), from about 5% to about 15% by weight aluminum oxide ($Al_2O_3$), from about 25% to about 50% by weight boron trioxide ($B_2O_3$), and from about 25% to about 50% by weight silicon dioxide ($SiO_2$). Ferro 3249 glass frit has a frit fusion point of 1024° C.; a frit flow point of 1246° C.; a specific gravity of 2.40 g/cm³; and a particle size of –325 mesh.

The most preferred inorganic phosphate compound is lithium metaphosphate ($LiPO_3$). Another example of an inorganic phosphate compound that can be used is potassium dihydrogen phosphate ($KH_2PO_4$).

There are several different methods of combining the components of the preferred embodiment to form a multi-component non-toxic accelerator. The components can be processed by any known dry mixing technique, which includes ball milling, jet milling, attrition milling, V-blending, etc. Another method of mixing the components is to process them by using any known wet mixing procedure. Wet mixing in water involves placing the components in water, mixing the solution, drying the mixture, and then grinding the mixture into a fine powder. Alternatively, the components can be processed by wet mixing in a solvent solution. This entails placing the components in a solvent, for example, mixing in isopropyl alcohol as a dispersing medium using a high density polyethylene jar and alumina balls, although there is no particular restriction on the liquid dispersing medium that can be used. The wet slurry produced is then dried and ground into a fine powder. Finally, the components can be dry mixed, wet mixed in a water solution, or wet mixed in a solvent solution, and then heated to a high temperature of between about 300° C. to about 1700° C., preferably between about 500° C. to about 700° C., thereby melt-mixing the components. The resulting powder melts into a chunk of glass-like material, which is then ground into a fine powder using, for example, a mortar and pestal, of no more than about 2 mm, with the preferred particle size being from about 0.1 to about 20 µm.

Tungsten oxide ($WO_3$), can be beneficially mixed with one or both of glass frit and/or an inorganic phosphate compound, as opposed to merely using tungsten oxide ($WO_3$) as the sole accelerator. Tungsten oxide ($WO_3$) has been used as a substitute for the traditional accelerator, vanadium oxide ($V_2O_5$), in cases where objections to the use of vanadium oxide ($V_2O_5$) powder existed, and/or vanadium oxide ($V_2O_5$) was unavailable. Substitution of tungsten oxide ($WO_3$) for vanadium oxide ($V_2O_5$) yielded adequate results, as tungsten oxide ($WO_3$) possesses similar decomposition capabilities. However, tungsten oxide ($WO_3$) performed beneficially only at higher temperatures and for a smaller range of samples. By combining tungsten oxide ($WO_3$) with one of glass frit and/or an inorganic phosphate compound, a multicomponent accelerator is produced that is both non-toxic and is useful for application at a broader range of temperatures, thus covering a broader range of samples.

The weight ratio of accelerators to each other when a multicomponent non-toxic accelerator is formed is not critical. The multicomponent accelerator can have any ratio in weight among the components. A more preferred range of accelerator components in a multicomponent accelerator comprises, for example, tungsten oxide or niobium pentoxide and lithium metaphosphate or glass frit, in a weight ratio from 40:1 to 10:1. In the most preferred embodiment, the ratio by weight of tungsten oxide and lithium metaphosphate is 20:1.

Tungsten oxide can be combined with one or both of the phosphate and glass frit components using any of the previously described mixing techniques (dry mixing; wet mixing in water; wet mixing in solvent; mixing followed by heat treatment).

Once it is determined which accelerator (either single component or multicomponent) is to be used for a particular analysis, the accelerator is then mixed with the substance to be analyzed. Any suitable mixing technique can be utilized. In the examples discussed below, Tobacco, the sample to be analyzed, is mixed with the chosen accelerator by hand blending the mixture of substance and accelerator using a spatula.

The ratio of accelerator to the substance to be analyzed is not critical, and can vary within usual ranges used in the art. Preferably, about 2 grams of accelerator is mixed with approximately 0.15 grams of the substance to be analyzed.

The non-toxic accelerators of the preferred embodiment are useful in testing for a broad range of particular elements in the elemental analysis of whatever substance is chosen for examination. The examples discussed below employ the non-toxic accelerators of the preferred embodiment in testing for sulfur content in samples of tobacco, barium sulfate ($BaSO_4$), and calcium sulfate ($CaSO_4$). The non-toxic accelerators of the preferred embodiment are also useful in testing for phosphorous, carbon, fluorine, chlorine, bromine, iodine, as well as other elements.

The non-toxic accelerators of the preferred embodiment are useful in a wide range of analytical instrumentation applications. The examples discussed below utilize the SC-444 carbon and sulfur analyzer (made by LECO Corporation), although any suitable instrumentation may be employed.

The general testing procedure is as follows. First, an appropriate amount of non-toxic accelerator (either single component or multicomponent) of the preferred embodiment would be mixed with a desired amount of the substance to be tested. The mixture is then placed in a suitable combustion container. The combustion container with its contents is then placed in the combustion analyzer and heated to a temperature of about 450° C. to about 1450° C. Certain photo-organic analyzing equipment exists that employs a combustion temperature of about 750° C. The SC-444 used in the examples discussed below has a combustion range of about 450° C. to about 1450° C., with the most preferred combustion temperature being about 1450° C. Once the sample is combusted, the gasses released are then analyzed for their elemental composition.

EXAMPLES

In the examples below, a suitable amount of the non-toxic accelerator of the preferred embodiment (either single component or multicomponent) was weighed into a ceramic boat with 0.15 grams of Tobacco (or barium sulfate, or calcium sulfate). The accelerator and the Tobacco (or barium sulfate, or calcium sulfate) were then hand blended using a spatula. Next, the ceramic boat with blended Tobacco and accelerator was pushed into a combustion tube of the SC-444 carbon and sulfur analyzer (made by LECO Corporation) and tested at a desired combustion range (in the examples the temperatures used are 1250° C., 1350° C., and 1450° C.) for sulfur determination. Although sulfur is used in the examples as the element being tested for, the non-toxic accelerators of the preferred embodiment are useful for analyzing a broad range of elements, including, but not limited to, phosphorous, carbon, fluorine, chlorine, bromine, and iodine. This procedure was employed to demonstrate that use of the non-toxic accelerators of the preferred embodiment would produce both (a) a large sulfur signal, indicating a completely analyzed result, and (b) a sulfur signal that came off in a relatively short period of time, indicating that addition of the non-toxic accelerators of the preferred embodiment enhances the analysis.

Example 1

Two grams of Ferro 3249 glass frit was weighed in a ceramic boat followed by 0.15 grams of Tobacco. Tobacco and glass frit were blended by hand using a spatula. The ceramic boat with blended Tobacco and glass frit was pushed into the combustion tube of the SC-444 at 1450° C. for sulfur determination. Most of the sulfur signal came off within approximately 90 seconds while a small amount of residual lasted until approximately 120 seconds. FIG. 1 shows the result of the sulfur signal as a function of analysis time.

Example 2

Figure 2:
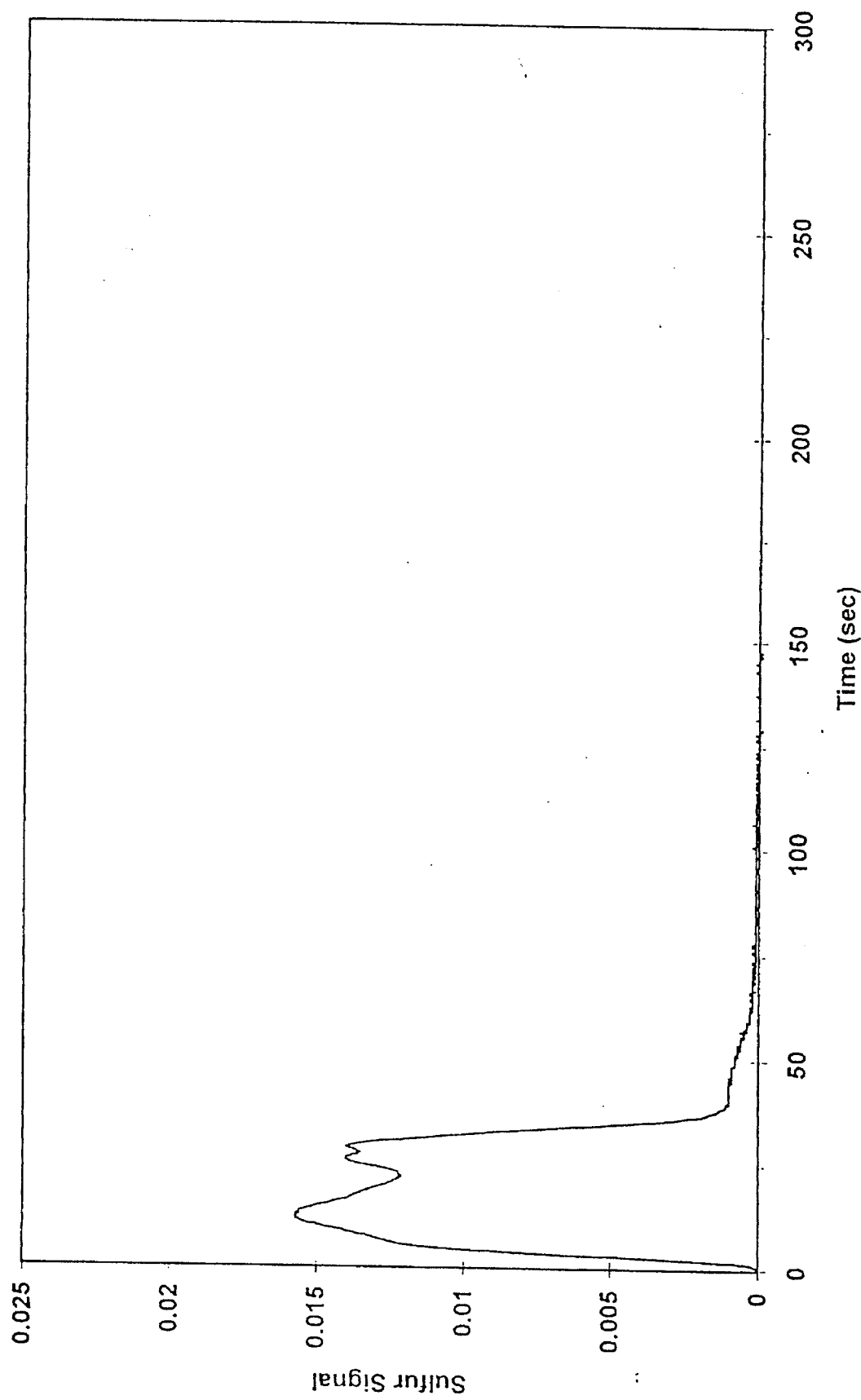
FIG. 2 shows the sulfur signal as a function of time for tobacco with lithium metaphosphate ($LiPO_3$) as the accelerator.

Two grams of lithium metaphosphate ($LiPO_3$) was weighed into a ceramic boat followed by 0.15 grams of Tobacco. Tobacco and lithium metaphosphate were blended by hand using a spatula. The ceramic boat with blended Tobacco and lithium metaphosphate was pushed into the combustion tube of the SC-444 at 1450° C. for sulfur determination. All of the sulfur signal came off within approximately 70 seconds. FIG. 2 shows the result of the sulfur signal as a function of analysis time.

Example 3

Figure 3:
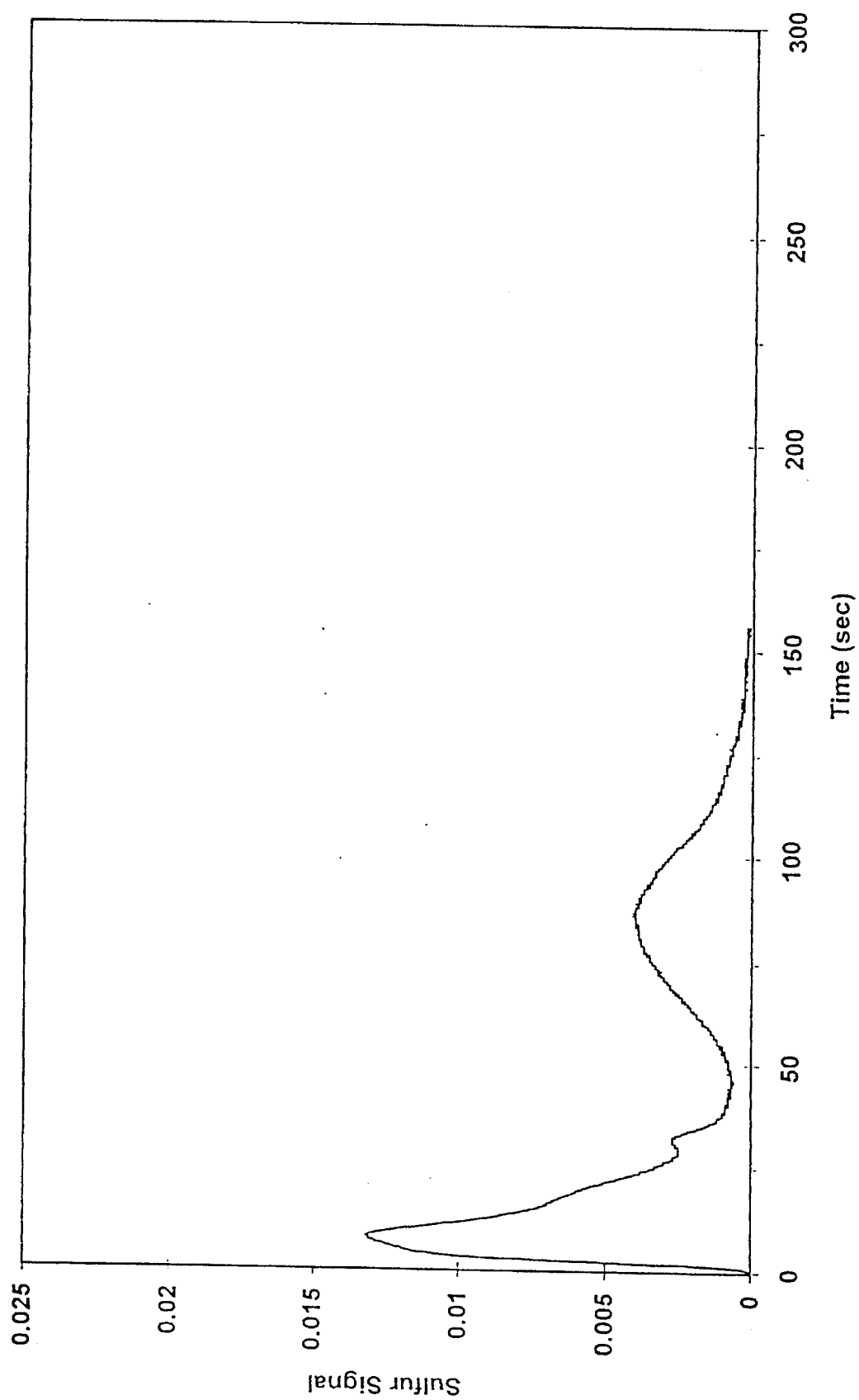
FIG. 3 shows the sulfur signal as a function of time for tobacco with niobium pentoxide ($Nb_2O_5$) as the accelerator.

Two grams of niobium pentoxide ($Nb_2O_5$) was weighed in the ceramic boat followed by 0.15 grams of tobacco. The ceramic boat with blended Tobacco and niobium pentoxide was pushed into the combustion tube of the SC-444 at 1450° C. for sulfur determination. All of the sulfur signal came off within approximately 150 seconds. FIG. 3 shows the result of the sulfur signal as a function of analysis time.

Figure 4:
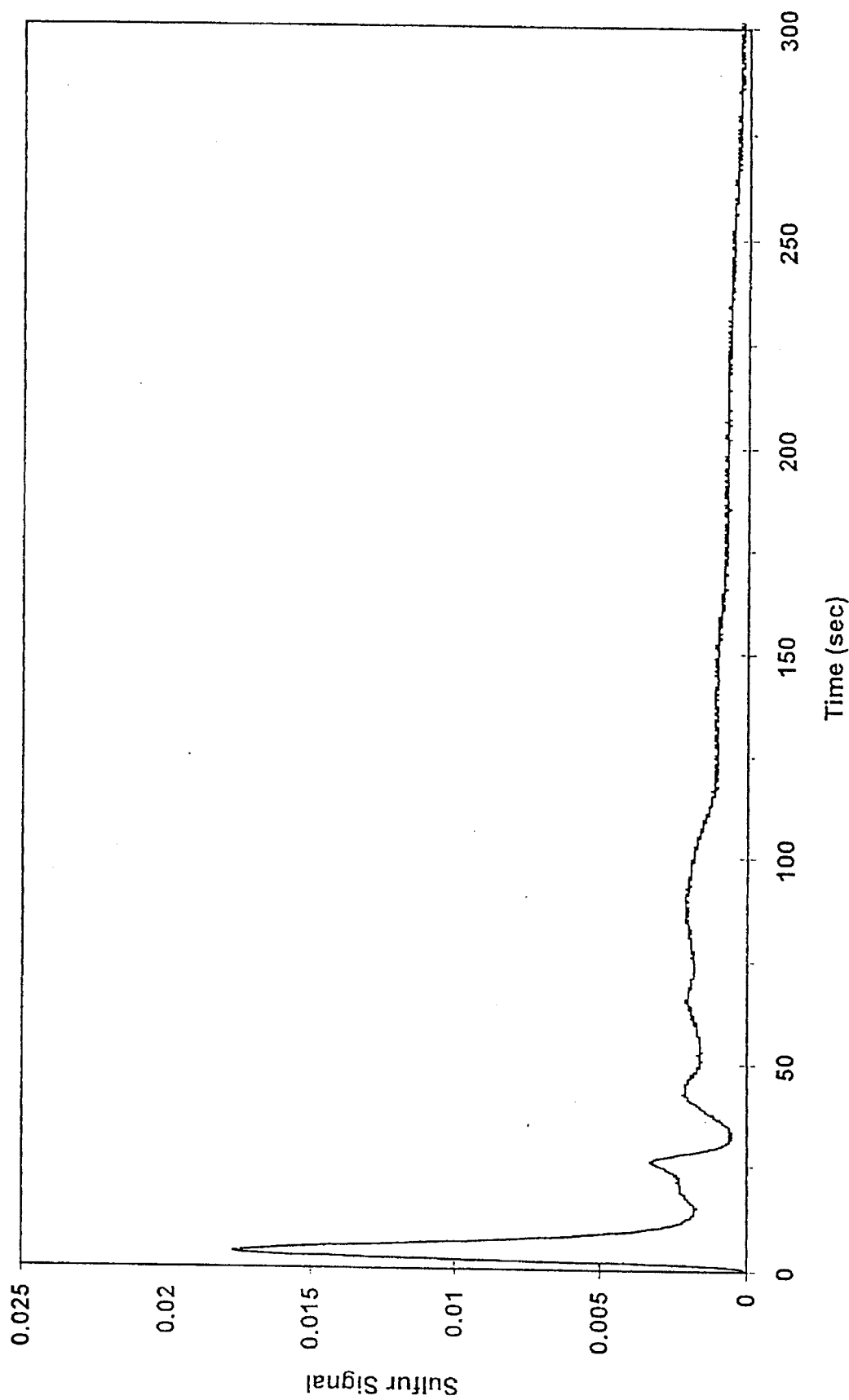
FIG. 4 shows the sulfur signal as a function of time for tobacco without any accelerator.

Example 4 - Comparative 0.15 grams of Tobacco was weighed in the ceramic boat without any accelerator. The ceramic boat with Tobacco was pushed into the combustion tube of the SC-444 at 1450° C. for sulfur determination as in example 1. The sulfur signal extends to approximately 300 seconds. FIG. 4 shows the result of the sulfur signal as a function of analysis time.

Example 5 - Comparative

Figure 5:
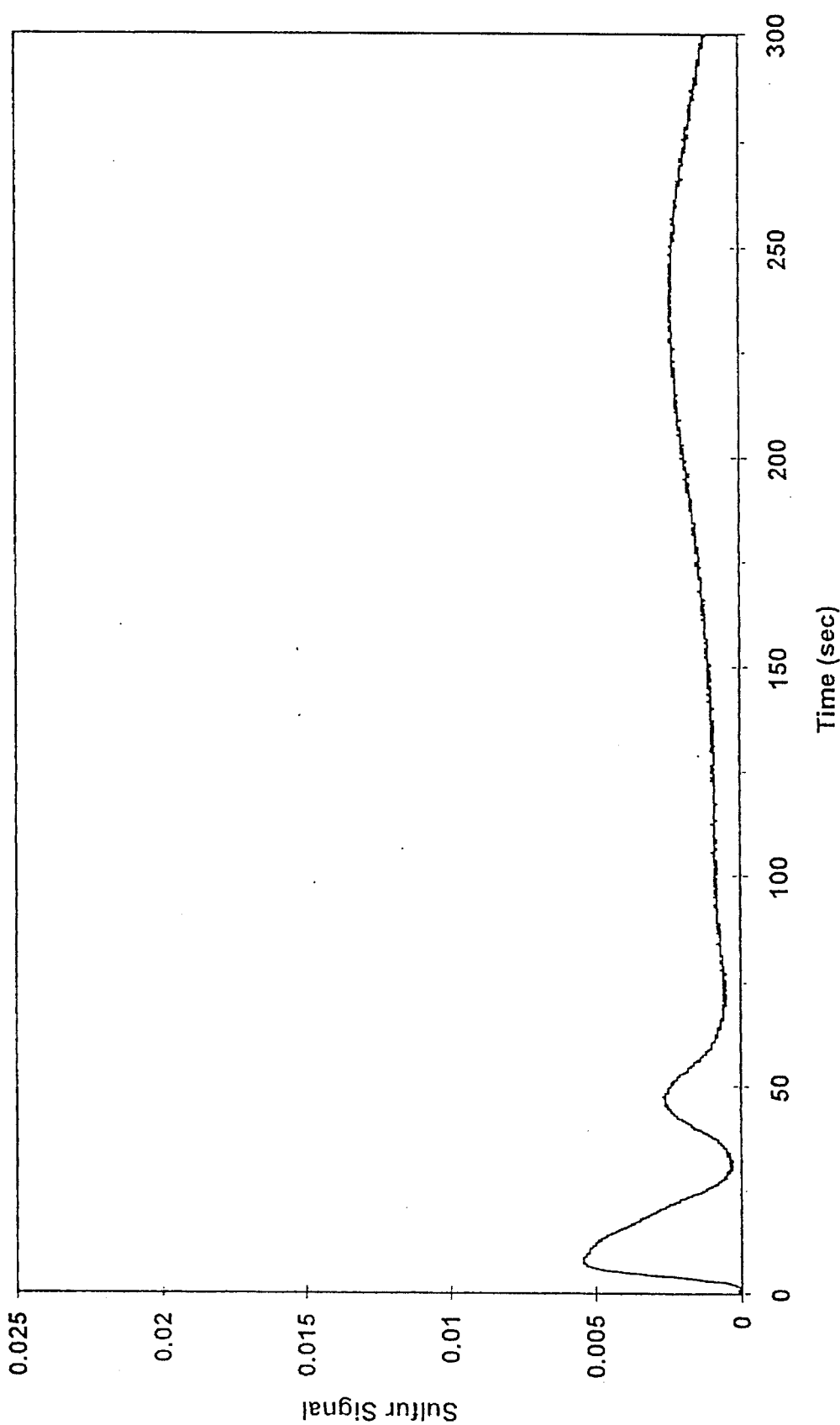
FIG. 5 shows the sulfur signal as a function of time for tobacco with zirconium oxide ($ZrO_2$) as the accelerator.

Two grams of zirconium oxide ($ZrO_2$) was weighed in the ceramic boat followed by 0.15 grams of Tobacco. The mixture and ceramic boat were prepared and analyzed for sulfur determination as in example 1. The primary sulfur peaks within 50 seconds were suppressed and the sulfur signal extended beyond 300 seconds. FIG. 5 shows the result of the sulfur signal as a function of analysis time.

Example 6 - Comparative

Figure 6:
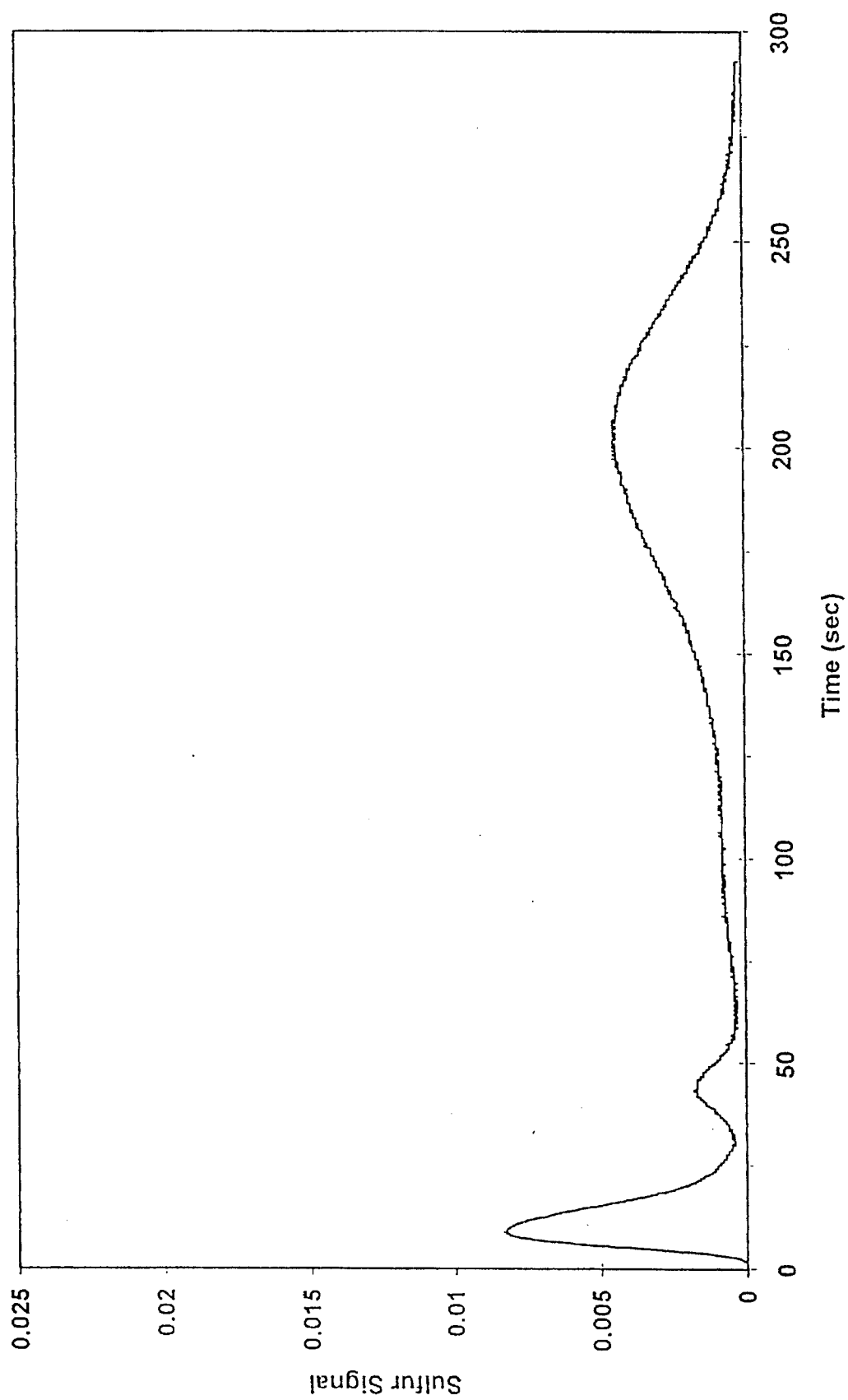
FIG. 6 shows the sulfur signal as a function of time for tobacco with aluminum oxide ($Al_2O_3$) as the accelerator.

Two grams of aluminum oxide ($Al_2O_3$) was weighed in the ceramic boat followed by 0.15 grams of tobacco. The mixture and ceramic boat were prepared and analyzed for sulfur determination as in example 1. The primary sulfur peaks within 50 seconds were suppressed and the sulfur signal extended beyond 300 seconds. FIG. 6 shows the result of the sulfur signal as a function of analysis time.

Example 7

Figure 7:
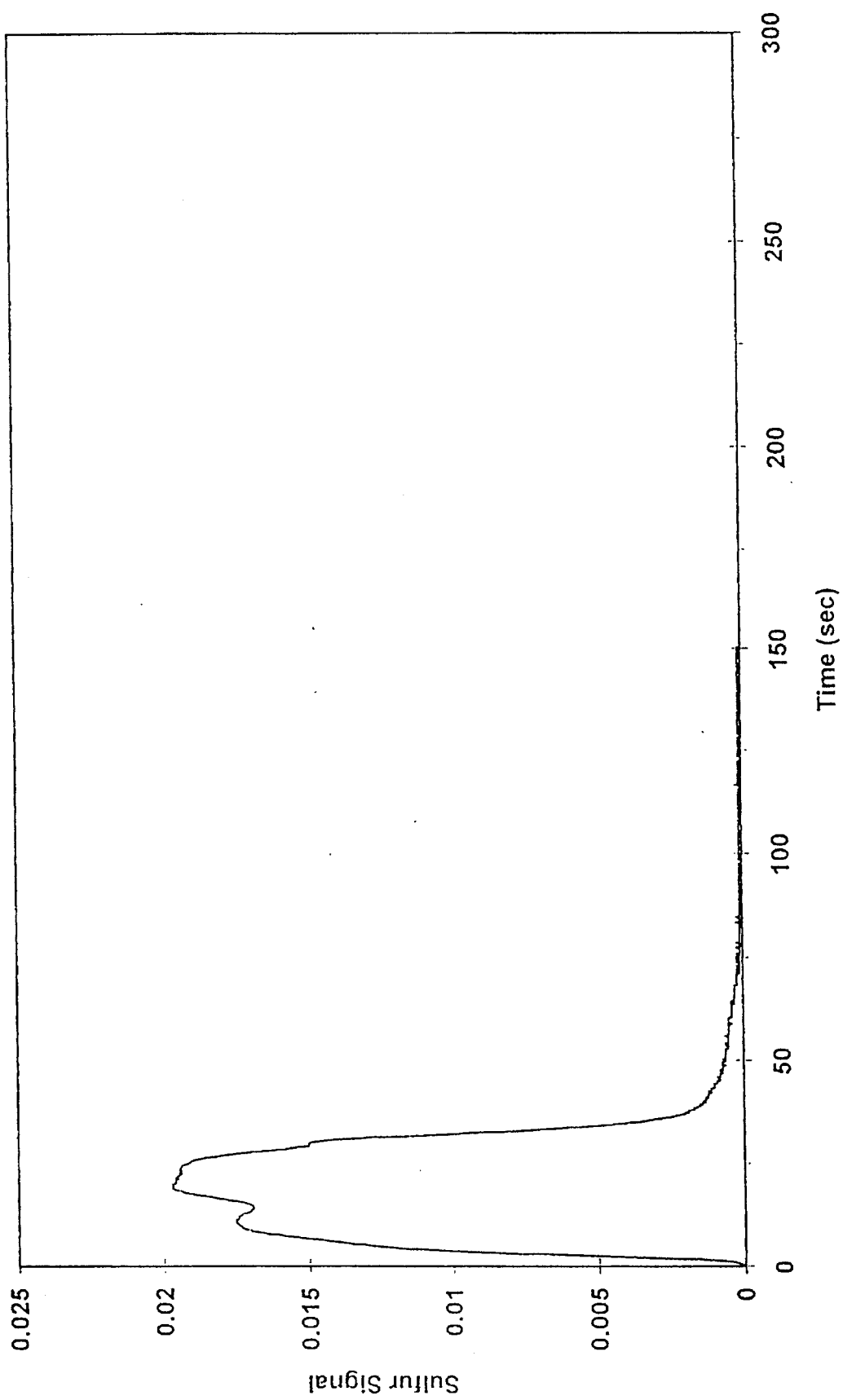
FIG. 7 shows the sulfur signal as a function of time for tobacco with a mixture of compound comprising niobium pentoxide ($Nb_2O_5$) and lithium metaphosphate ($LiPO_3$) with 2:1 weight ratio as the accelerator.

1.5 grams of the same lithium metaphosphate ($LiPO_3$) as used in example 2 and 1.5 grams of the same niobium pentoxide ($Nb_2O_5$) as used in example 3 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 75 seconds. FIG. 7 shows the result of the sulfur signal as a function of analysis time.

Example 8

Figure 8:
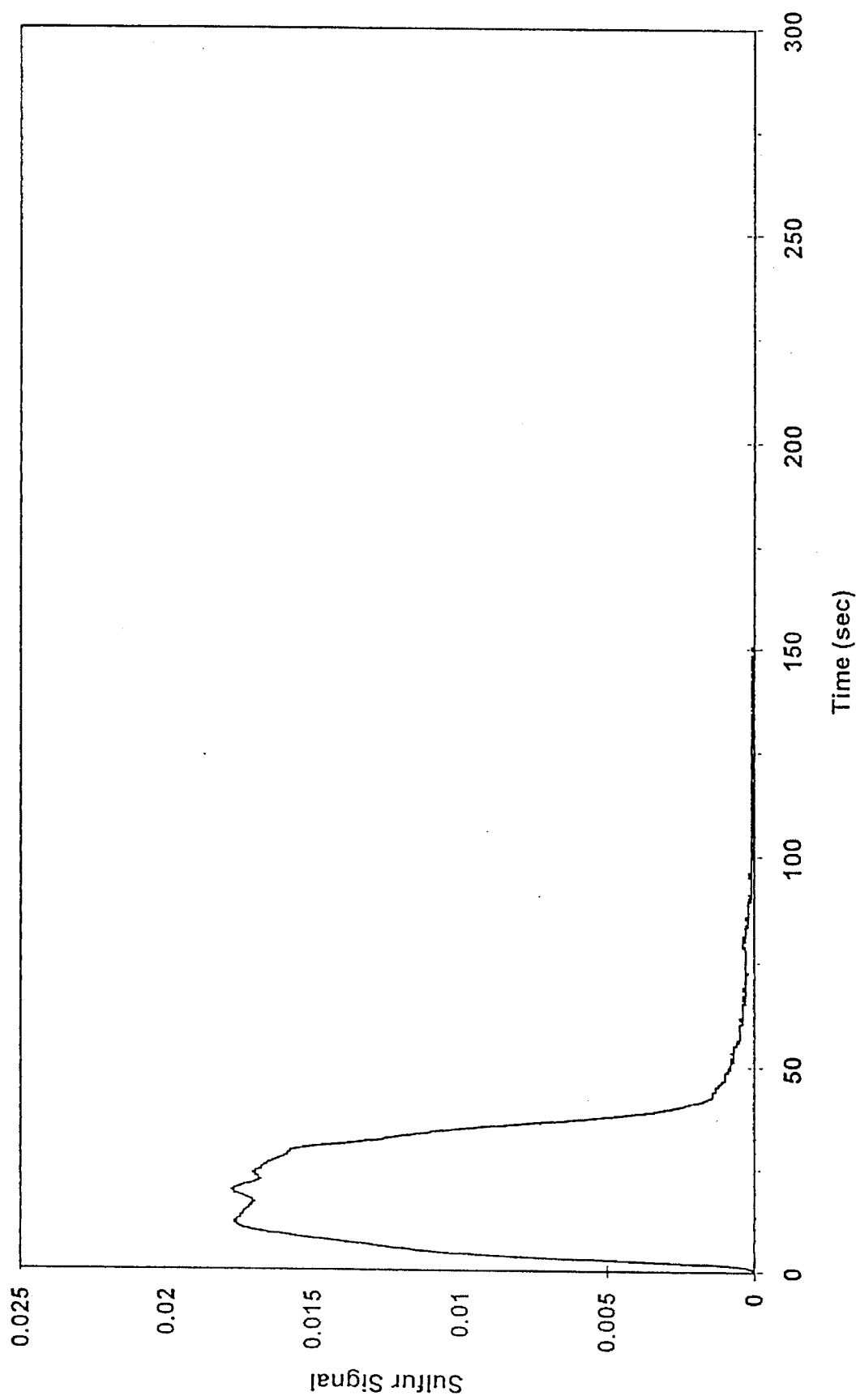
FIG. 8 shows the sulfur signal as a function of time for tobacco with a mixture of compound comprising tungsten oxide ($WO_3$) and lithium metaphosphate ($LiPO_3$) with 5:6 weight ratio as the accelerator.

1.5 grams of tungsten oxide ($WO_3$) and 1.8 grams of the same lithium metaphosphate ($LiPO_3$) used in example 2 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 100 seconds. FIG. 8 shows the result of the sulfur signal as a function of analysis time.

Example 9

Figure 9:
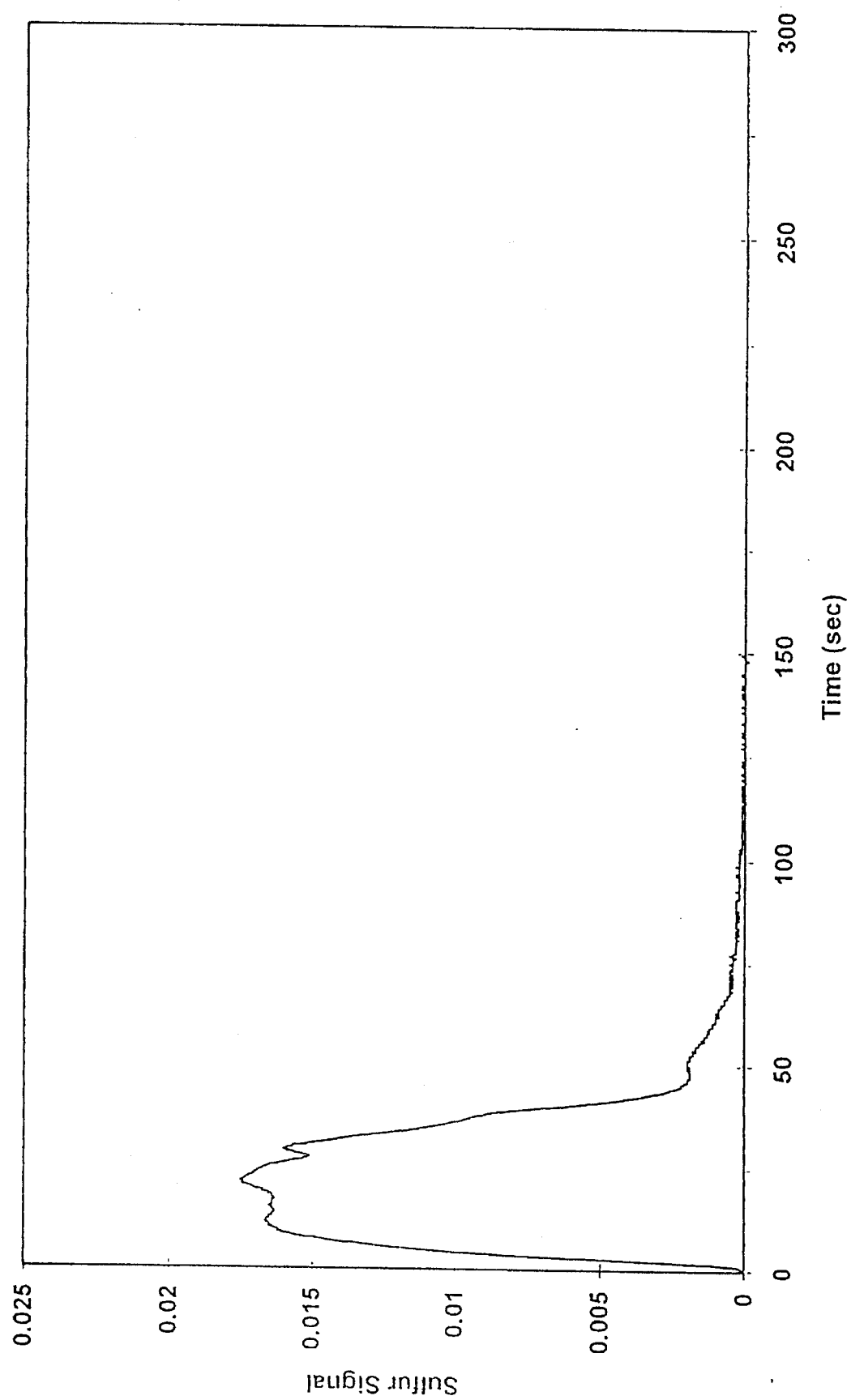
FIG. 9 shows the sulfur signal as a function of time for tobacco with a mixture of compound comprising tungsten oxide ($WO_3$) and lithium metaphosphate ($LiPO_3$) with 5:2 weight ratio as the accelerator.

Two grams of tungsten oxide ($WO_3$) and 0.8 grams of the same lithium metaphosphate ($LiPO_3$) used in example 2 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 110 seconds. FIG. 9 shows the result of the sulfur signal as a function of analysis time.

Example 10

Figure 10:
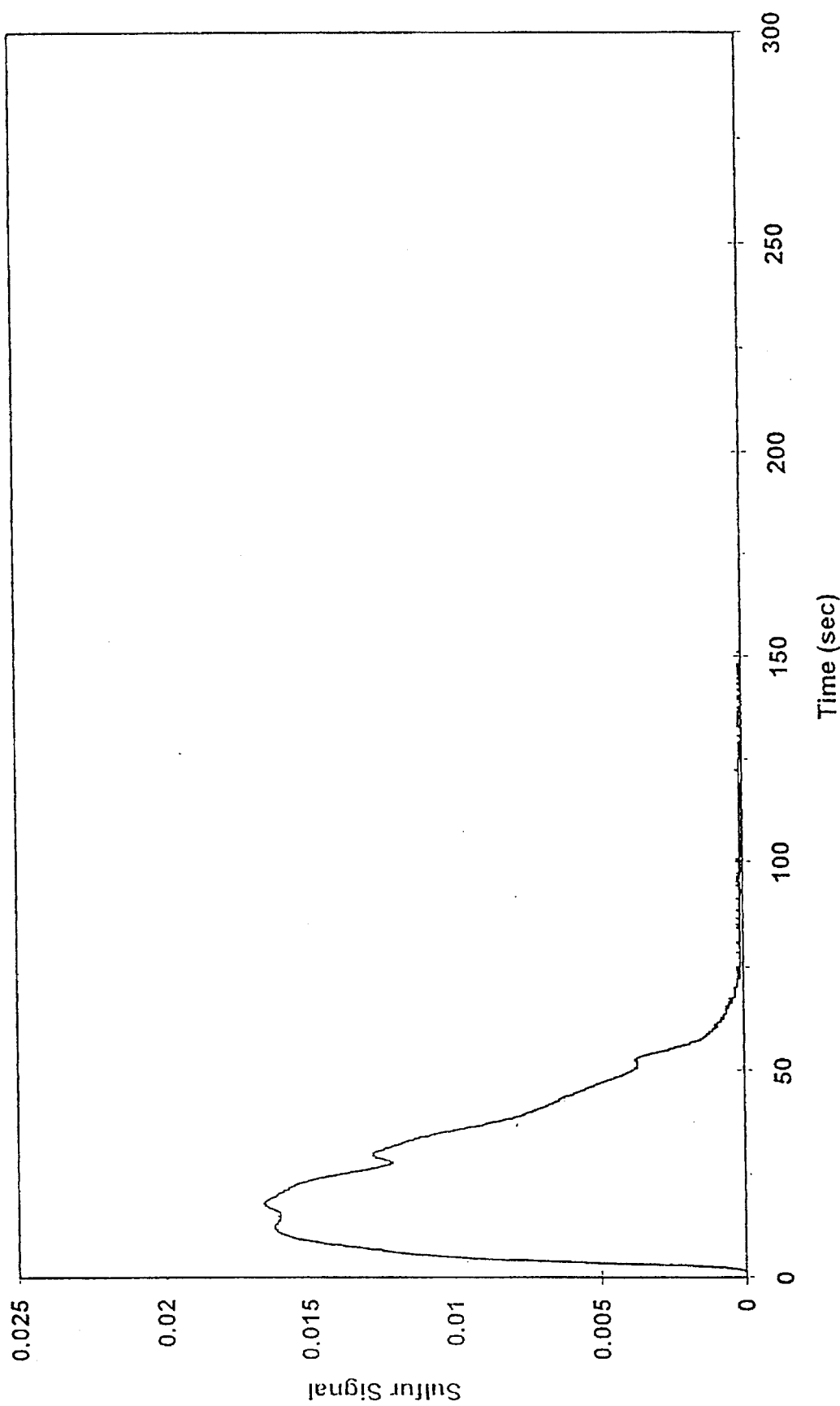
FIG. 10 shows the sulfur signal as a function of time for tobacco with a mixture of compound comprising tungsten oxide ($WO_3$) and lithium metaphosphate ($LiPO_3$) with 5:1 weight ratio as the accelerator.

Four grams of tungsten oxide ($WO_3$) and 0.8 grams of the same lithium metaphosphate ($LiPO_3$) used in example 2 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 75 seconds. FIG. 10 shows the result of the sulfur signal as a function of analysis time.

Example 11

Figure 11:
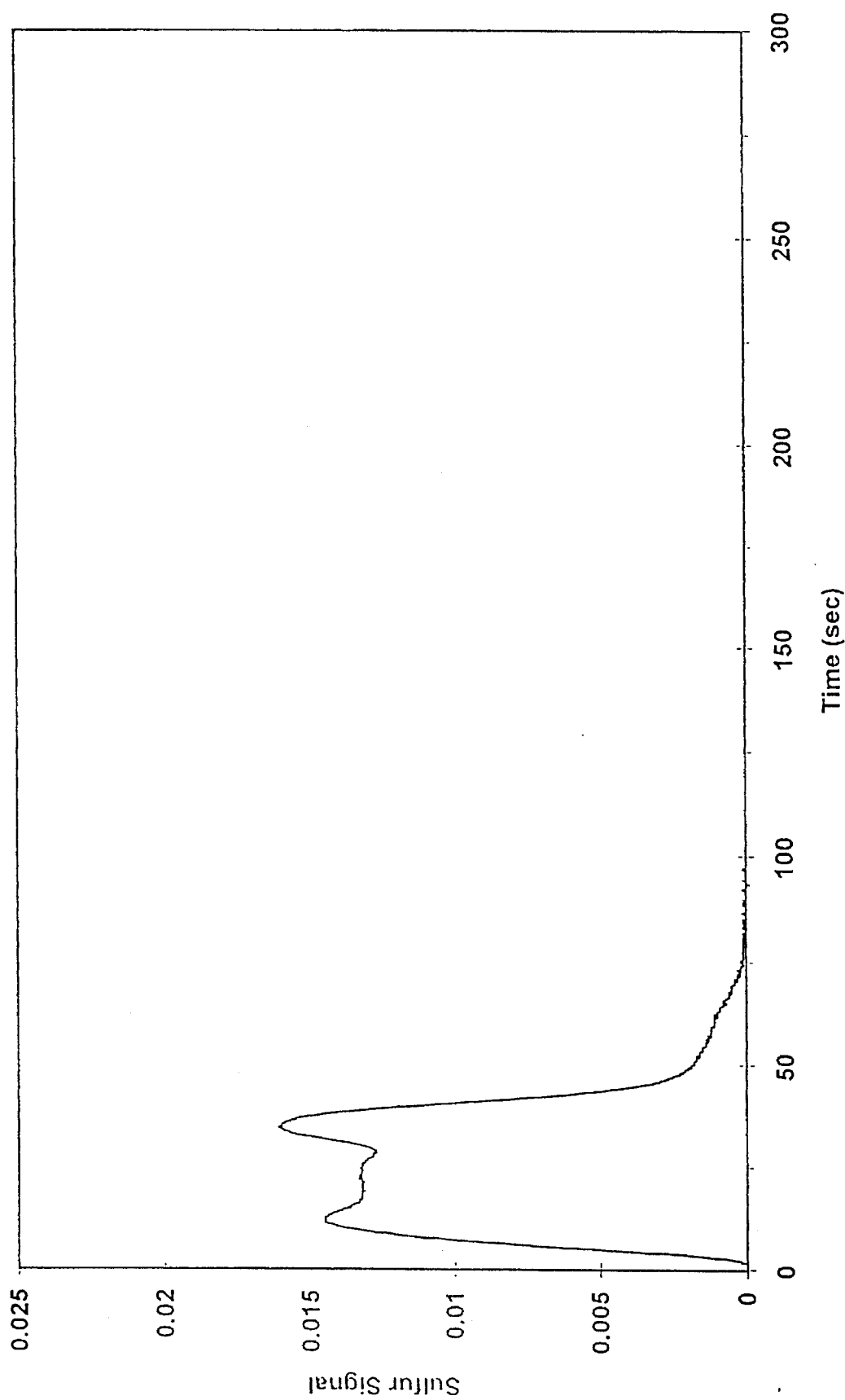
FIG. 11 shows the sulfur signal as a function of time for tobacco with a mixture of compound comprising tungsten oxide ($WO_3$) and lithium metaphosphate ($LiPO_3$) with 20:1 weight ratio as the accelerator.

Five grams of tungsten oxide ($WO_3$) and 0.25 grams of the same lithium metaphosphate ($LiPO_3$) used in example 2 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 75 seconds. FIG. 11 shows the result of the sulfur signal as a function of analysis time.

Example 12

Figure 12:
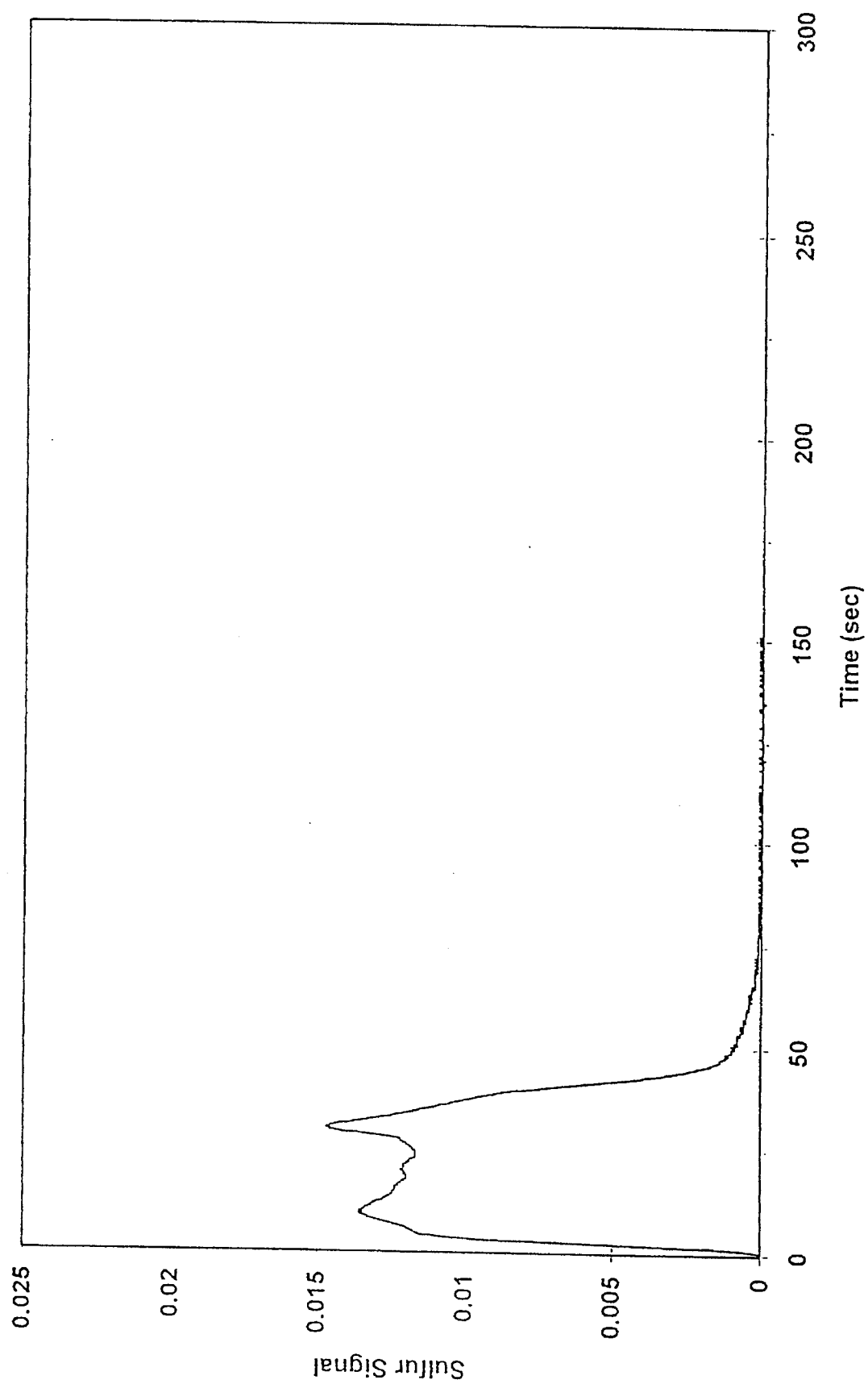
FIG. 12 shows the sulfur signal as a function of time for tobacco with a mixture of compound comprising tungsten oxide ($WO_3$) and potassium dihydrogen phosphate ($KH_2PO_4$) with 10:1 weight ratio as the accelerator.

Five grams of tungsten oxide ($WO_3$) as used in example 2 and 0.5 grams of potassium dihydrogen phosphate ($KH_2PO_4$) were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 75 seconds. FIG. 12 shows the result of the sulfur signal as a function of analysis time.

Example 13

Figure 13:
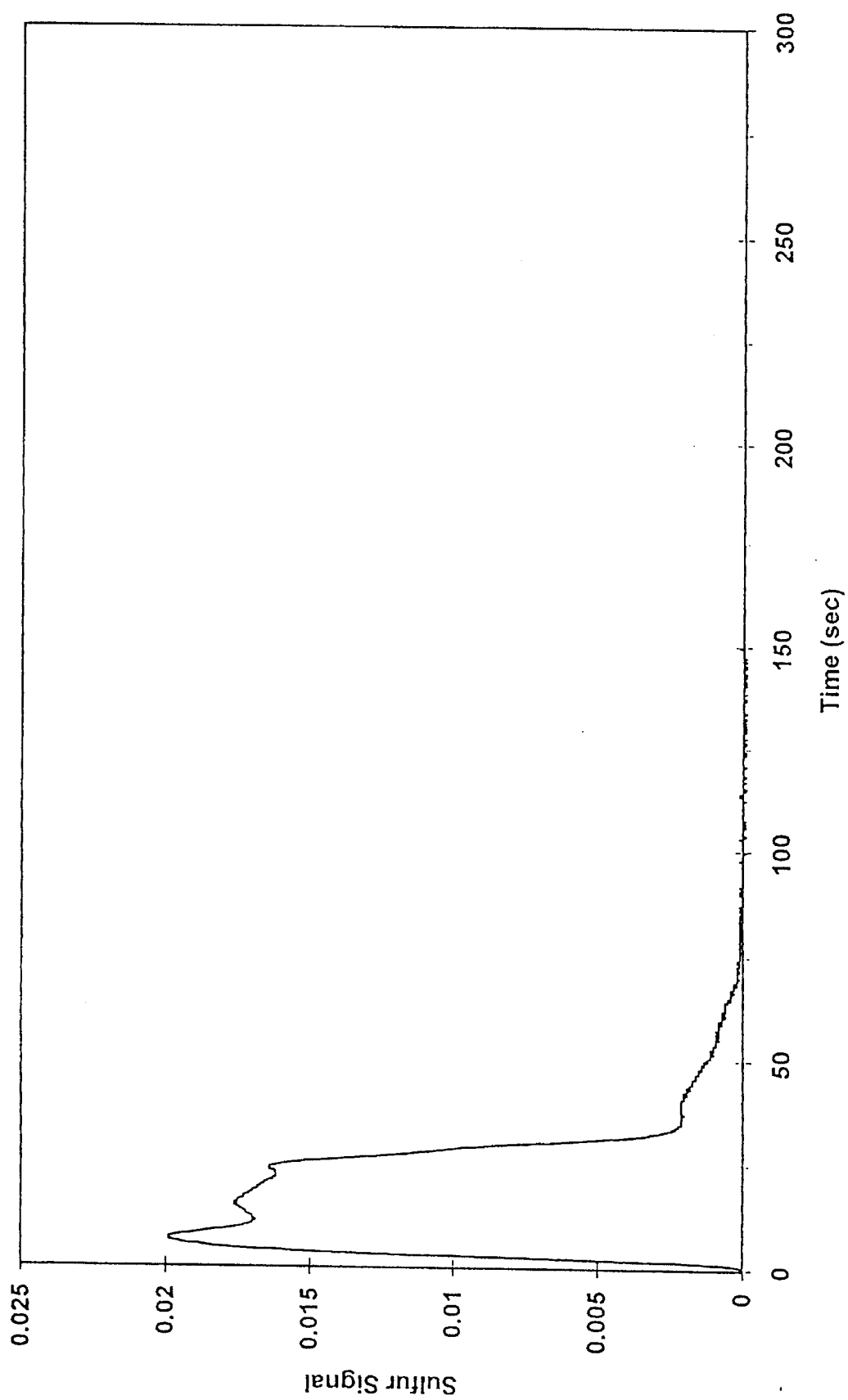
FIG. 13 shows the sulfur signal as a function of time for tobacco with a mixture of compound comprising tungsten oxide ($WO_3$), lithium metaphosphate ($LiPO_3$), and sodium tetraborate ($NaBO_4$) with 4:2:1 weight ratio as the accelerator.

Two grams of tungsten oxide ($WO_3$) and one gram of the same lithium metaphosphate ($LiPO_3$) used in example 2, and 0.5 grams of sodium tetraborate ($NaBO_4$) were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. All of the sulfur signal came off within approximately 80 seconds. FIG. 13 shows the result of the sulfur signal as a function of analysis time.

Example 14 - Comparative

Figure 14:
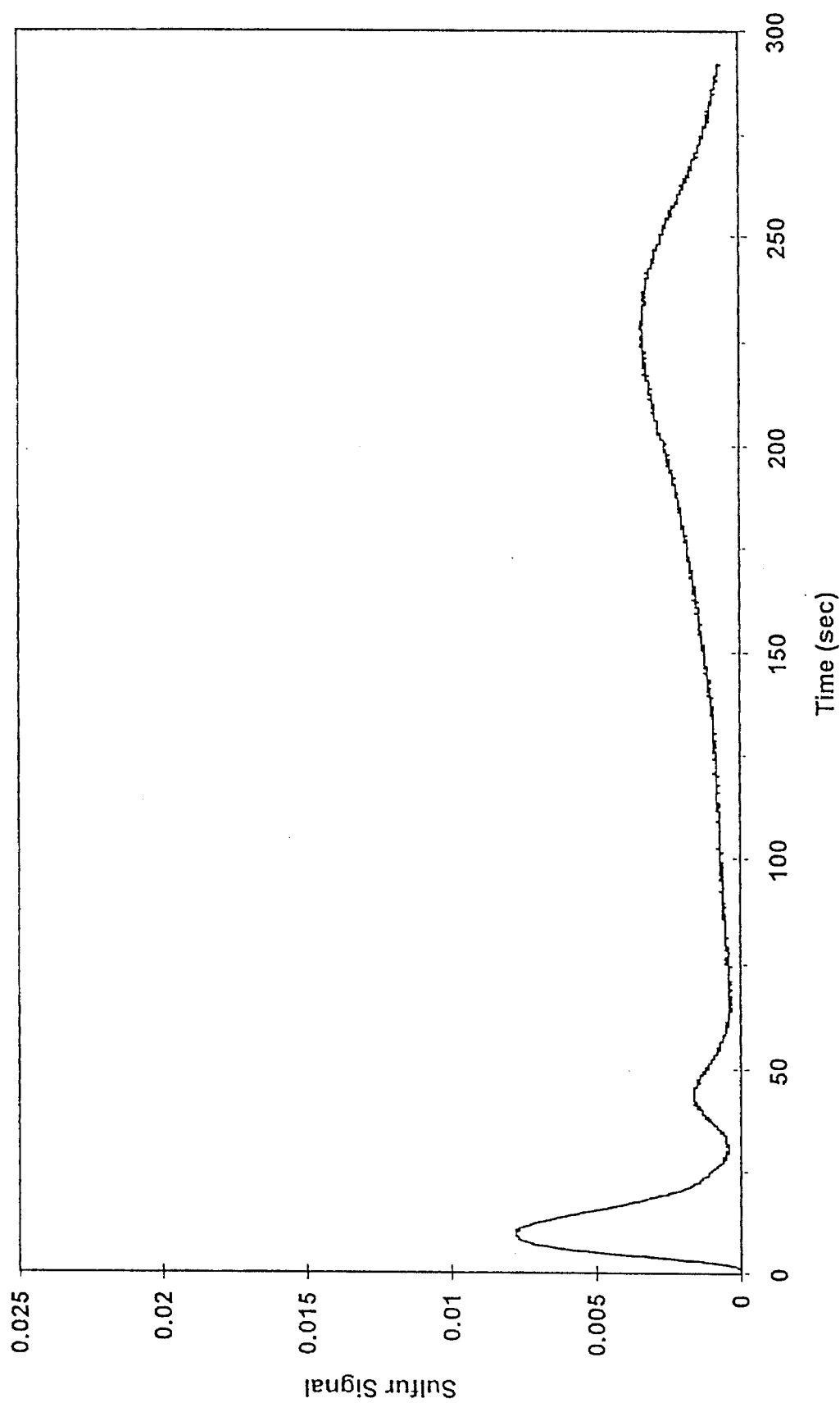
FIG. 14 shows the sulfur signal as a function of time for tobacco with zirconium oxide ($ZrO_2$) and aluminum oxide ($Al_2O_3$) with 1:1 weight ratio as the accelerator.

One gram of the same zirconium oxide ($ZrO_2$) as used in example 5 and one gram of the same aluminum oxide ($Al_2O_3$) as used in example 6 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1450° C. for sulfur determination. Not only was the first major peak suppressed, the sulfur signal was also extended to beyond 300 seconds. FIG. 14 shows the result of the sulfur signal as a function of analysis time.

Example 15

Figure 15:
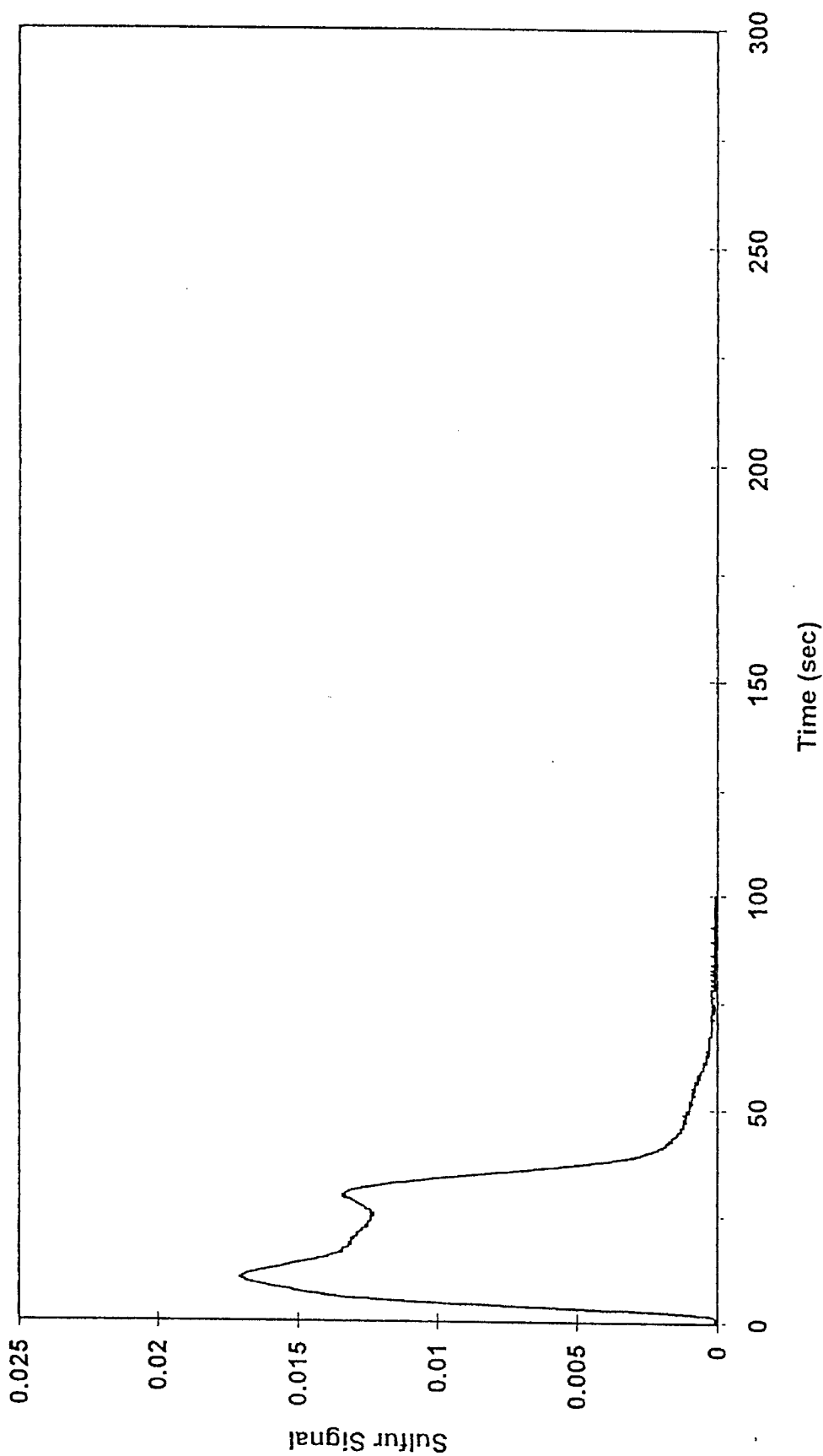
FIG. 15 shows the sulfur signal as a function of time for tobacco with a mixture of compound comprising tungsten oxide ($WO_3$) and lithium metaphosphate ($LiPO_3$) with 20:1 weight ratio wet-mixed in isopropyl alcohol as the accelerator.

Ninety grams of tungsten oxide ($WO_3$) and 4.5 grams of the same lithium metaphosphate ($LiPO_3$) used in example 2 were uniformly mixed in isopropyl alcohol as a dispersing medium using a high density polyethylene jar and alumina balls. The wet slurry was dried at 70° C. for 24 hours before using a mortar and pestal to grind to a fine powder. Five grams of the ground fine powder was weighed into a ceramic boat followed by 0.15 grams of Tobacco. Tobacco and the mixture were blended by hand using a spatula. The ceramic boat with blended Tobacco and ground fine mixture was pushed into the combustion tube of the SC-444 at 1450° C. for sulfur determination. All of the sulfur signal came off within approximately 70 seconds. FIG. 15 shows the result of the sulfur signal as a function of analysis time.

Example 16

Figure 16:
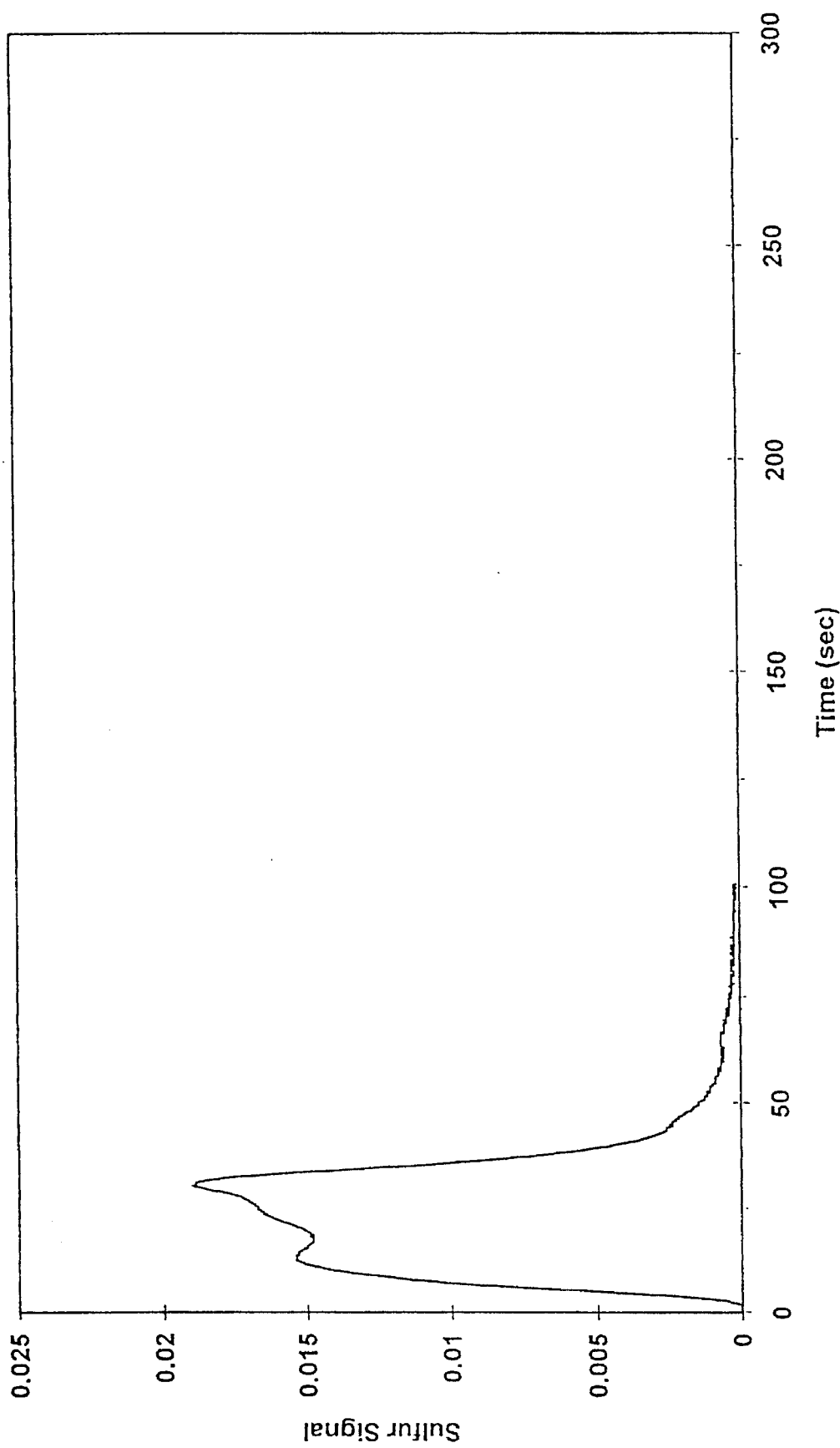
FIG. 16 shows the sulfur signal as a function of time for tobacco with a mixture of compound comprising tungsten oxide ($WO_3$) and lithium metaphosphate ($LiPO_3$) with 5:6 weight ratio and followed by a reaction at 650° C. for 20 minutes as the accelerator.

Thirty grams of mixture from example 8 was loaded into an alumina crucible and covered by a lid. The crucible was then heated to 650° C. for 20 minutes in an air atmosphere at a heating rate of approximately 40° C./minute. The resulting powder melted into a greenish chunk of glass which was then ground into a fine powder by using the mortar and pestal. Four grams of this ground fine powder was weighed into a ceramic boat followed by 0.15 grams of Tobacco. Tobacco and the greenish glass powder were blended by hand using a spatula. The ceramic boat with blended Tobacco and ground fine mixture was pushed into the combustion tube of the SC-444 at 1450° C. for sulfur determination. All of the sulfur signal came off within approximately 75 seconds. FIG. 16 shows the result of the sulfur signal as a function of analysis time.

Example 17

Figure 17:
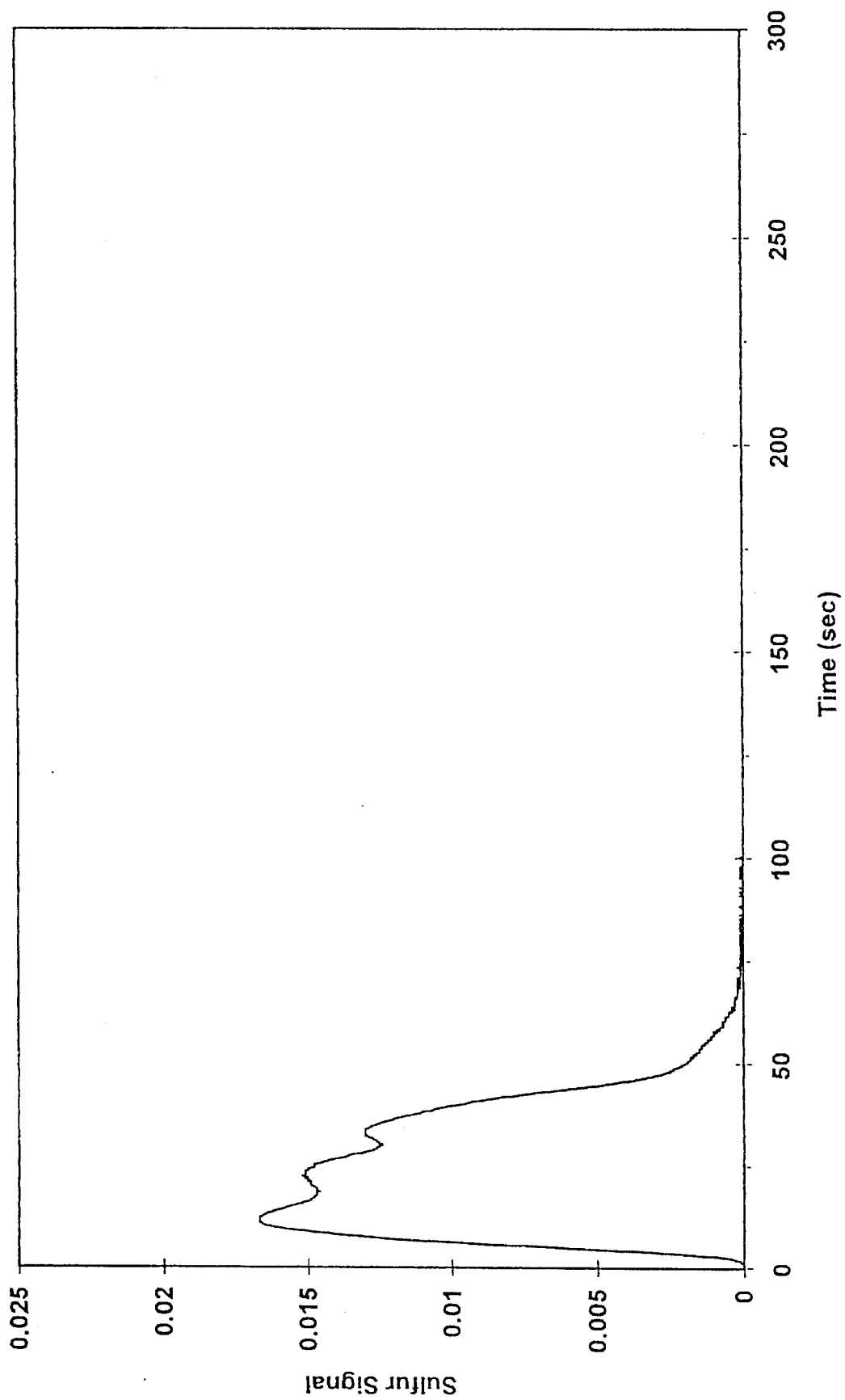
FIG. 17 shows the sulfur signal as a function of time for tobacco with a mixture of compound comprising tungsten oxide ($WO_3$) and lithium metaphosphate ($LiPO_3$) with 20:1 weight ratio wet-mixed in isopropyl alcohol and followed by a reaction at 700° C. for 5 minutes as the accelerator.

Thirty grams of the same mixture used in example 15 was loaded into an alumina crucible and covered by a lid. The crucible was then heated to 700° C. for 5 minutes in an air atmosphere at a heating rate of approximately 40° C./minute. The resulting powder melted into a greenish chunk of glass which was then ground into a fine powder by using the mortar and pestal. Five grams of this ground fine powder was weighed into a ceramic boat followed by 0.15 grams of Tobacco. Tobacco and the greenish glass powder were blended by hand using a spatula. The ceramic boat with blended Tobacco and ground fine mixture was pushed into the combustion tube of the SC-444 at 1450° C. for sulfur determination. All of the sulfur signal came off within approximately 75 seconds. FIG. 17 shows the result of the sulfur signal as a function of analysis time.

Example 18

Figure 18:
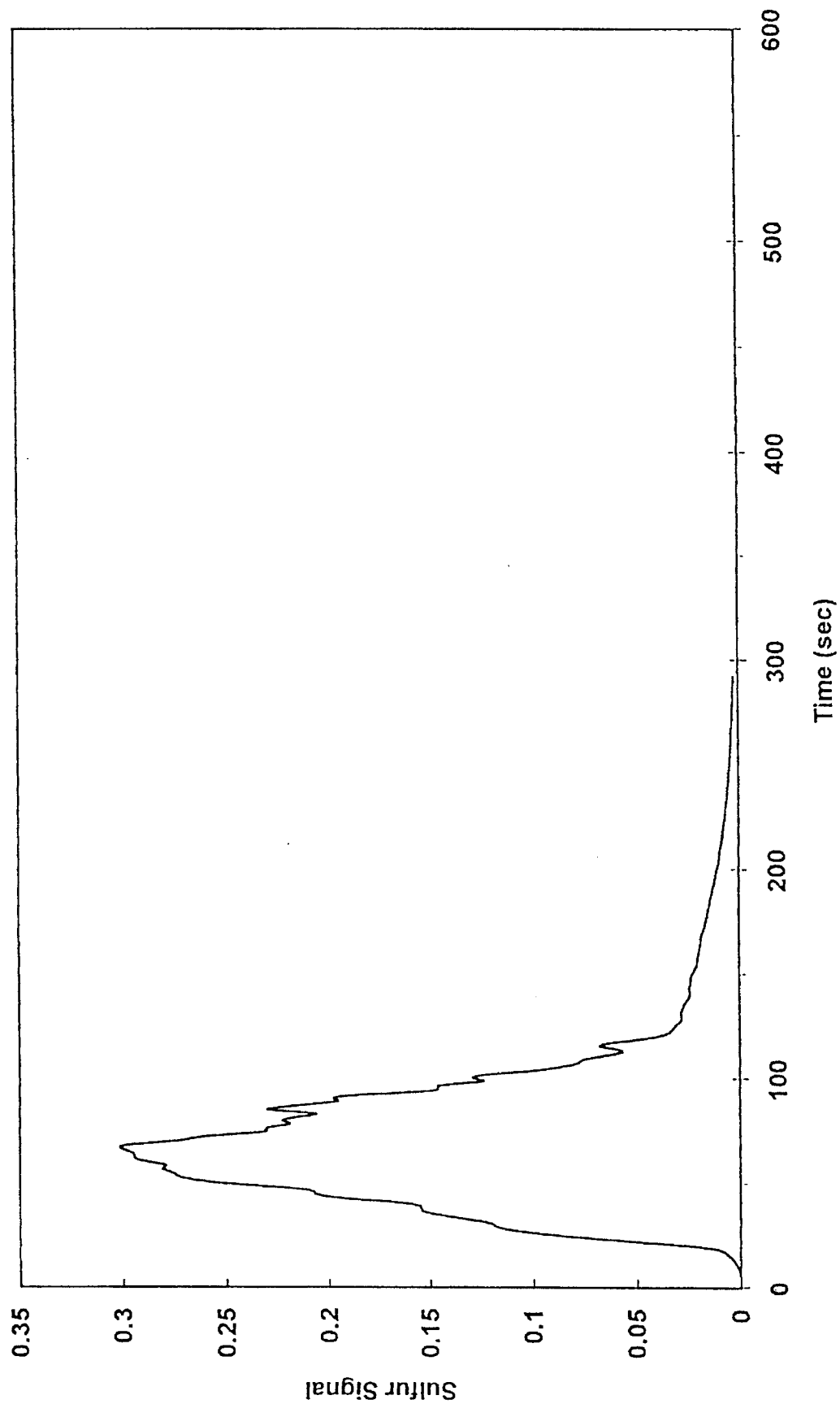
FIG. 18 shows the sulfur signal as a function of time for barium sulfate ($BaSO_4$) with lithium metaphosphate ($LiPO_3$) as the accelerator.

Five grams of the same lithium metaphosphate ($LiPO_3$) used in example 2 was weighed into a ceramic boat followed by 0.15 grams of barium sulfate ($BaSO_4$). The chemical bonds of sulfur in barium sulfate are much stronger than those in tobacco, and therefore harder to dissociate. Barium sulfate was substituted for tobacco as the sample to be tested to demonstrate that the non-toxic accelerators of the preferred embodiment would function sufficiently even in substances that are more difficult to analyze. Barium sulfate and lithium metaphosphate were blended by hand using a spatula. The ceramic boat with blended barium sulfate and lithium metaphosphate was pushed into the combustion tube of the SC-444 at 1450° C. for sulfur determination. All of the sulfur signal came off within approximately 300 seconds. FIG. 18 shows the result of the sulfur signal as a function of analysis time.

Example 19

Figure 19:
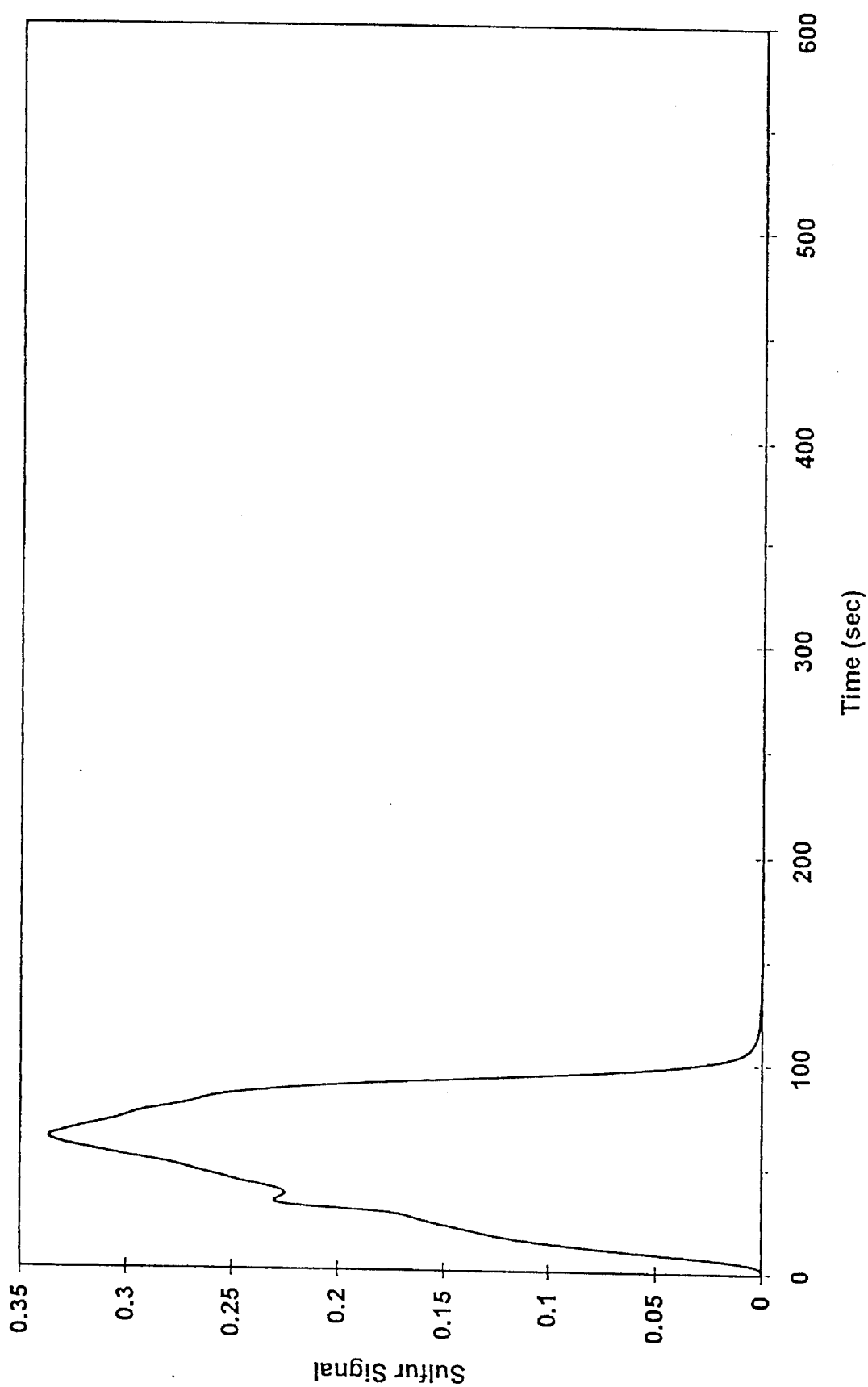
FIG. 19 shows the sulfur signal as a function of time for barium sulfate ($BaSO_4$) with a mixture of compound comprising tungsten oxide ($WO_3$) and lithium metaphosphate ($LiPO_3$) with 20:1 weight ratio as the accelerator.

Five grams of tungsten oxide ($WO_3$) and 0.25 grams of the same lithium metaphosphate ($LiPO_3$) used in example 2 were uniformly dry mixed in a mortar and pestal. The mixture was added in a ceramic boat followed by 0.15 grams of barium sulfate ($BaSO_4$). Barium sulfate was ground to fine powder before adding into the ceramic boat. Barium sulfate and the mixture were blended by hand using a spatula. The ceramic boat with blended Tobacco and mixture was pushed into the combustion tube of the SC-444 at 1450° C. for sulfur determination. All of the sulfur signal came off within approximately 120 seconds. FIG. 19 shows the result of the sulfur signal as a function of analysis time.

Figure 20:
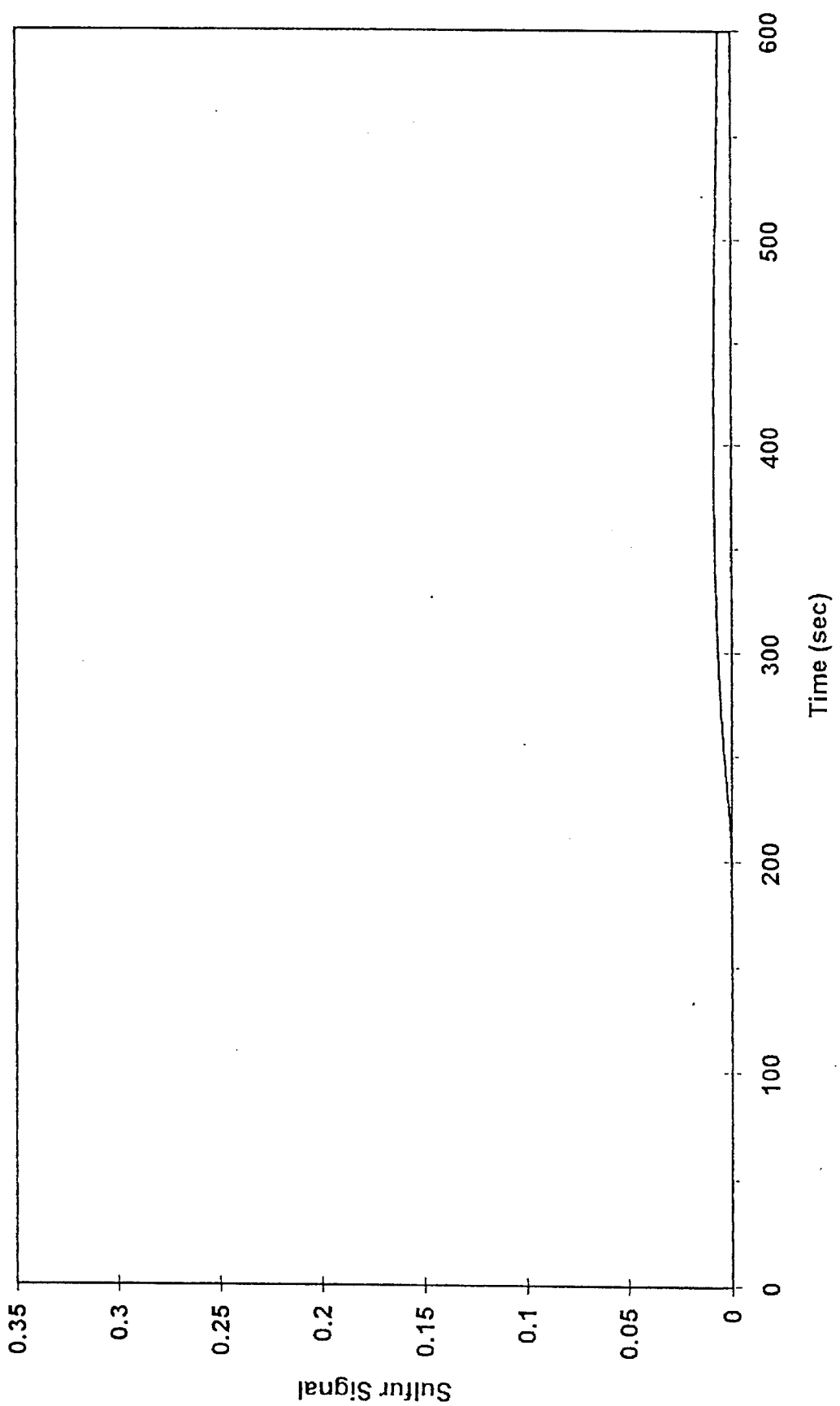
FIG. 20 shows the sulfur signal as a function of time for barium sulfate ($BaSO_4$) without any accelerator.

Example 20 - Comparative 0.15 grams of barium sulfate ($BaSO_4$) was weighed into a ceramic boat. The ceramic boat with barium sulfate was pushed into the combustion tube of the SC-444 at 1450° C. for sulfur determination. No sulfur signal was detected until approximately 200 seconds and only a small amount of sulfur signal came off even after 600 seconds. FIG. 20 shows the result of the sulfur signal as a function of analysis time.

Example 21

Figure 21:
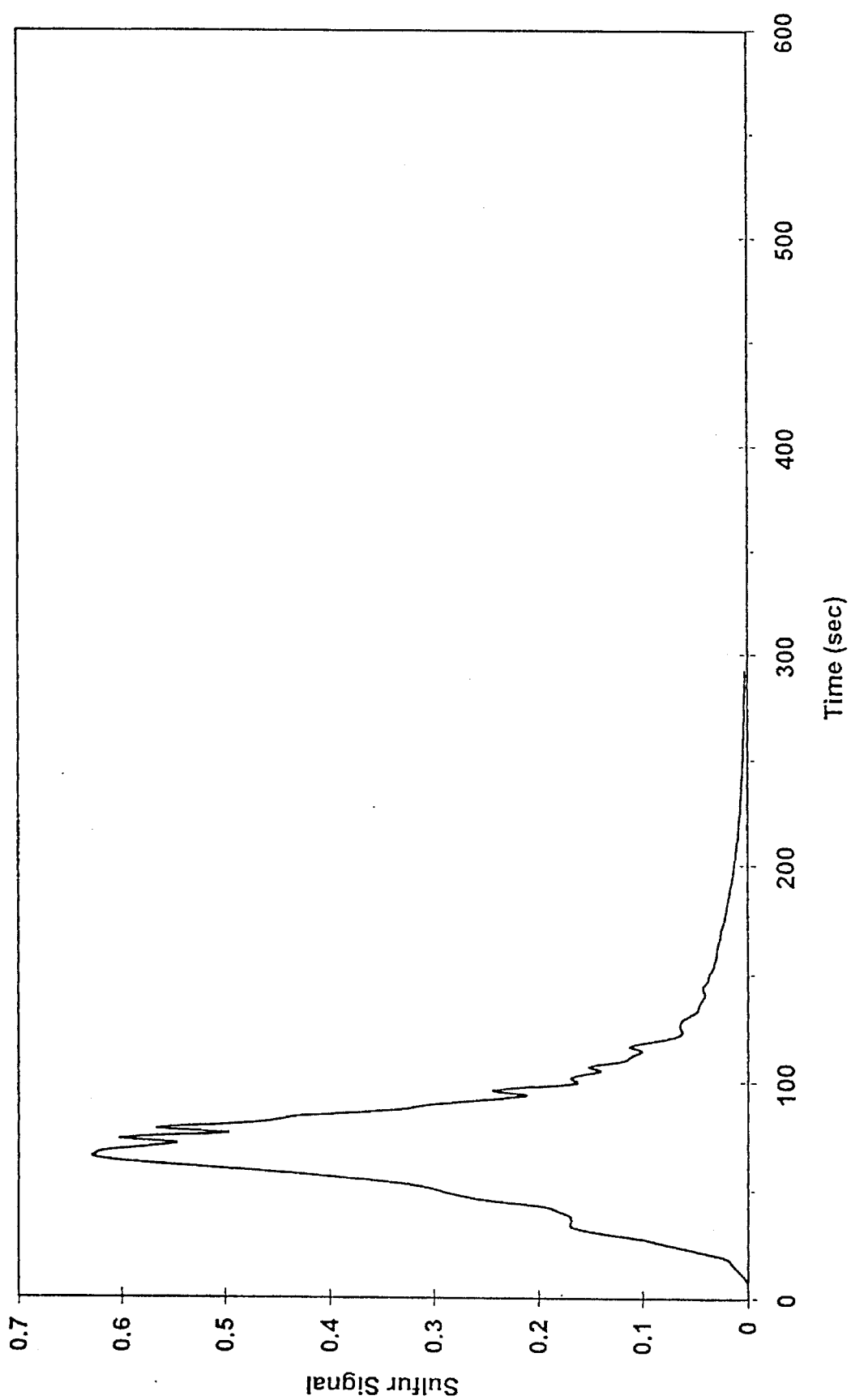
FIG. 21 shows the sulfur signal as a function of time for calcium sulfate ($CaSO_4$) with lithium metaphosphate ($LiPO_3$) as the accelerator.

Five grams of the same lithium metaphosphate ($LiPO_3$) used in example 2 was weighed into a ceramic boat followed by 0.15 grams of calcium sulfate ($CaSO_4$). Again, the chemical bonds of sulfur are much stronger in calcium sulfate than they are in Tobacco. Calcium sulfate and lithium metaphosphate were blended by hand using a spatula. The ceramic boat with blended barium sulfate and lithium metaphosphate was pushed into the combustion tube of the SC-444 at 1450° C. for sulfur determination. All of the sulfur signal came off within approximately 270 seconds. FIG. 21 shows the result of the sulfur signal as a function of analysis time.

Example 22

Figure 22:
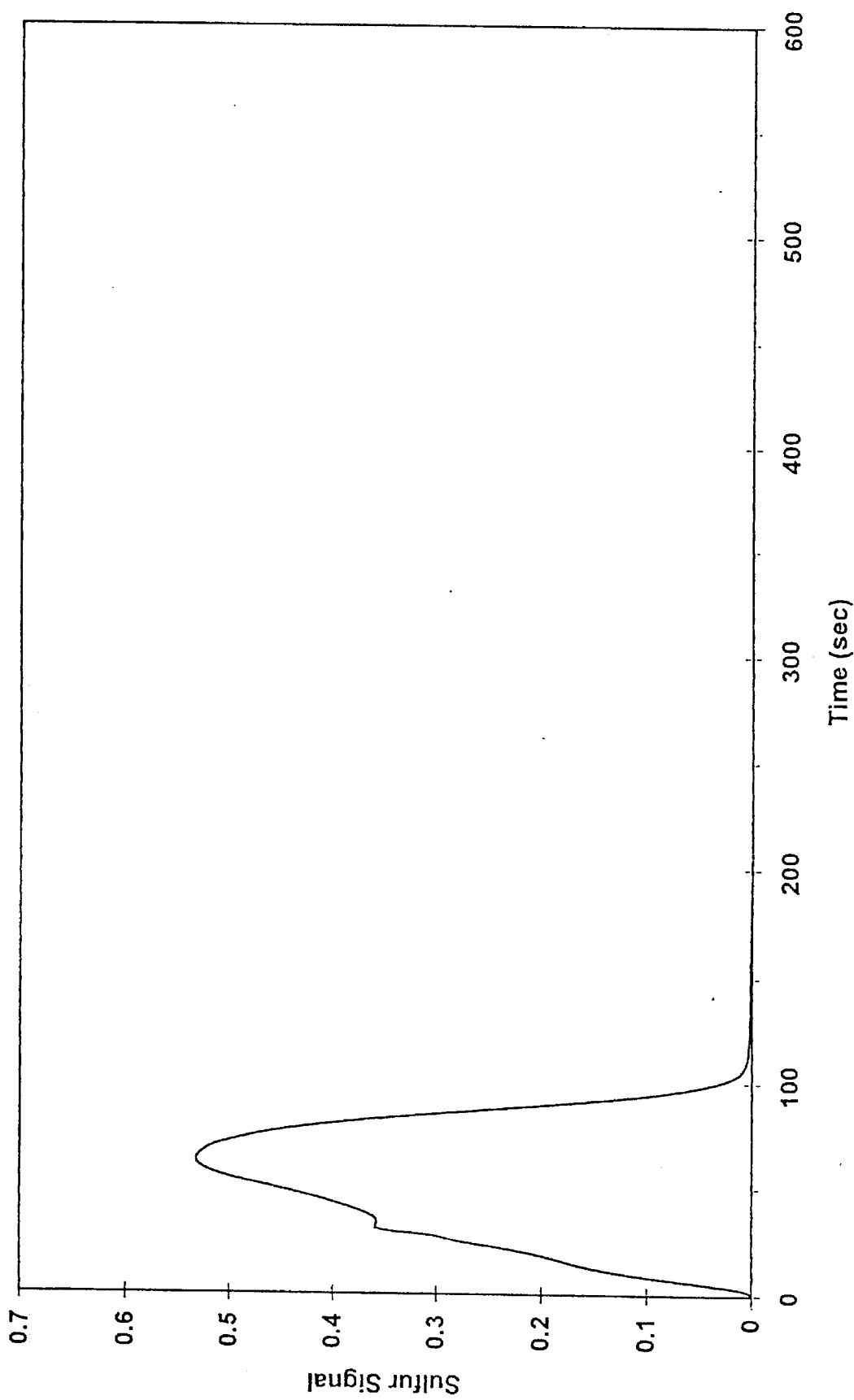
FIG. 22 shows the sulfur signal as a function of time for calcium sulfate ($CaSO_4$) with a mixture of compound comprising tungsten oxide ($WO_3$) and lithium metaphosphate ($LiPO_3$) with 20:1 weight ratio as the accelerator.

Five grams of tungsten oxide ($WO_3$) and 0.25 grams of the same lithium metaphosphate ($LiPO_3$) used in example 2 were uniformly dry mixed in a mortar and pestal. The mixture was added in a ceramic boat followed by 0.15 grams of calcium sulfate ($CaSO_4$). Calcium sulfate and the mixture were blended by hand using a spatula. The ceramic boat with blended calcium sulfate and mixture was pushed into the combustion tube of the SC-444 at 1450° C. for sulfur determination. All of the sulfur signal came off within approximately 120 seconds. FIG. 22 shows the result of the sulfur signal as a function of analysis time.

Figure 23:
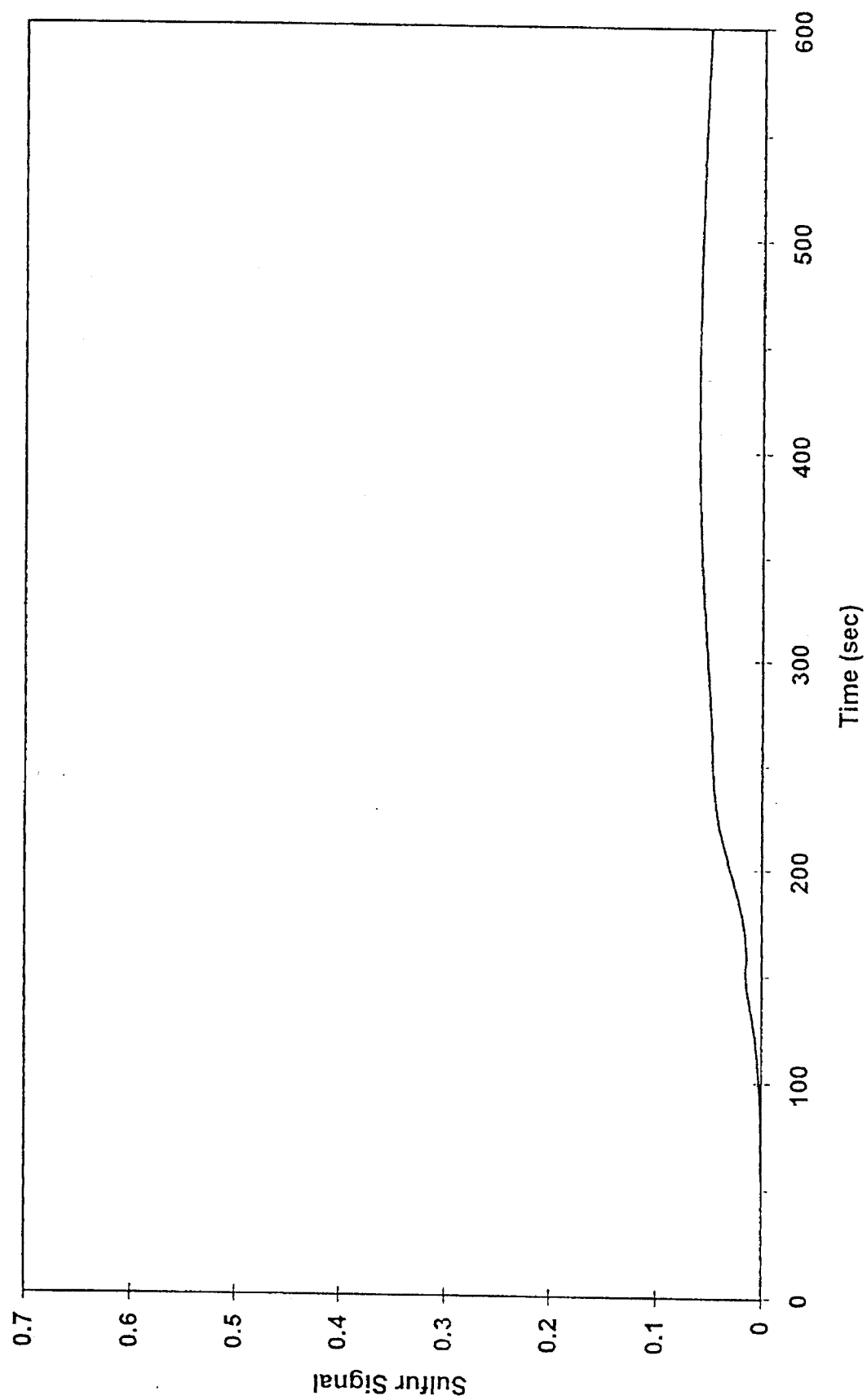
FIG. 23 shows the sulfur signal as a function of time for calcium sulfate ($CaSO_4$) without any accelerator.

Example 23 - Comparative 0.15 grams of calcium sulfate ($CaSO_4$) was weighed into a ceramic boat. The ceramic boat with calcium sulfate was pushed into the combustion tube of the SC-444 at 450° C. for sulfur determination. No sulfur signal was detected until approximately 100 seconds and the sulfur signal was extended to even after 600 seconds. FIG. 23 shows the result of the sulfur signal as a function of analysis time.

Example 24

Figure 24:
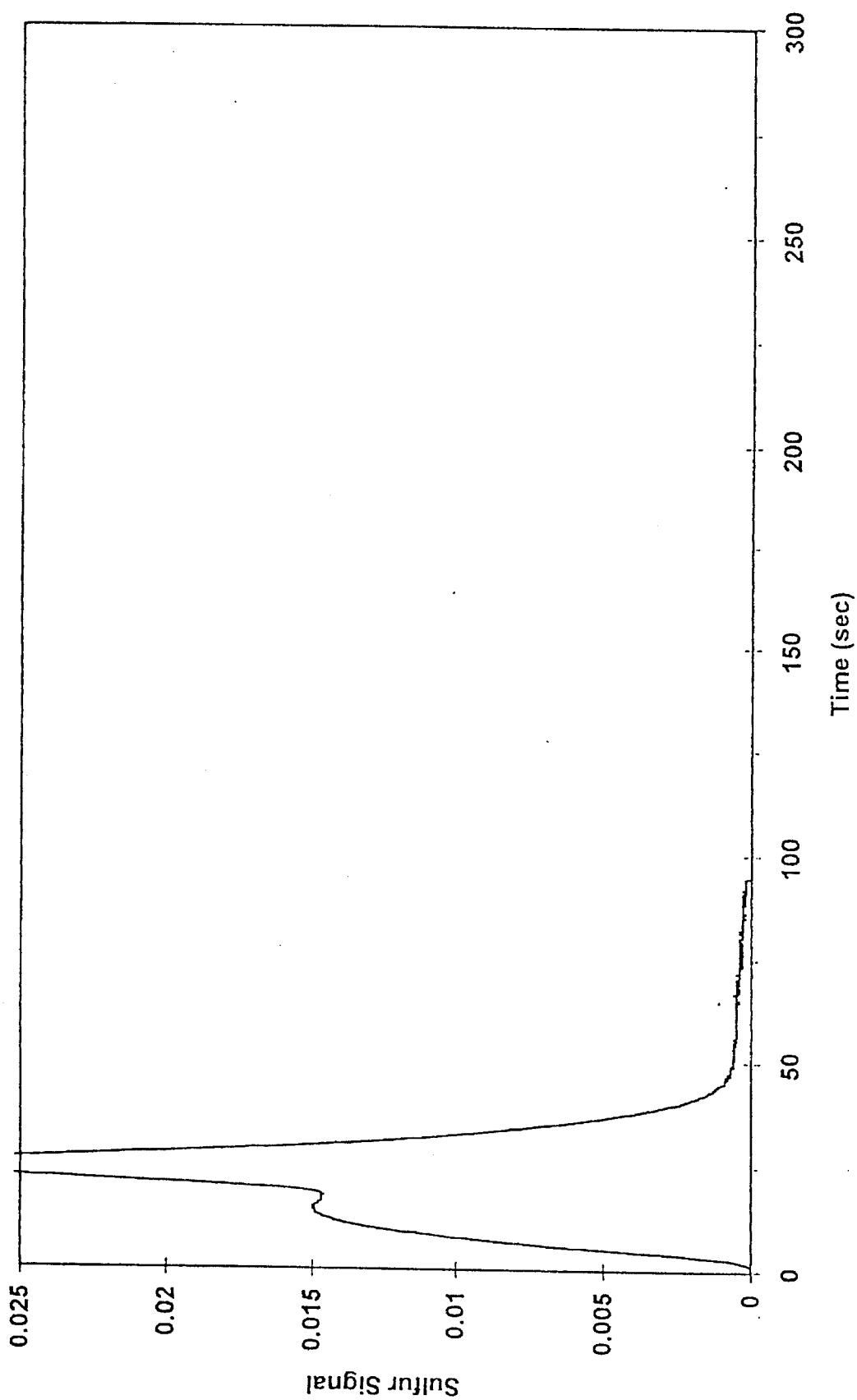
FIG. 24 shows the sulfur signal as a function of time for tobacco with lithium metaphosphate ($LiPO_3$) as the accelerator tested at 1350° C.

Two grams of the same lithium metaphosphate ($LiPO_3$) used in example 2 was weighed into a ceramic boat followed by 0.15 grams of Tobacco. Tobacco and lithium metaphosphate were blended by hand using a spatula. The ceramic boat with blended Tobacco and lithium metaphosphate was pushed into the combustion tube of the SC-444 at 1350° C. for sulfur determination. All of the sulfur signal came off within approximately 90 seconds. FIG. 24 shows the result of the sulfur signal as a function of analysis time.

Example 25

Figure 25:
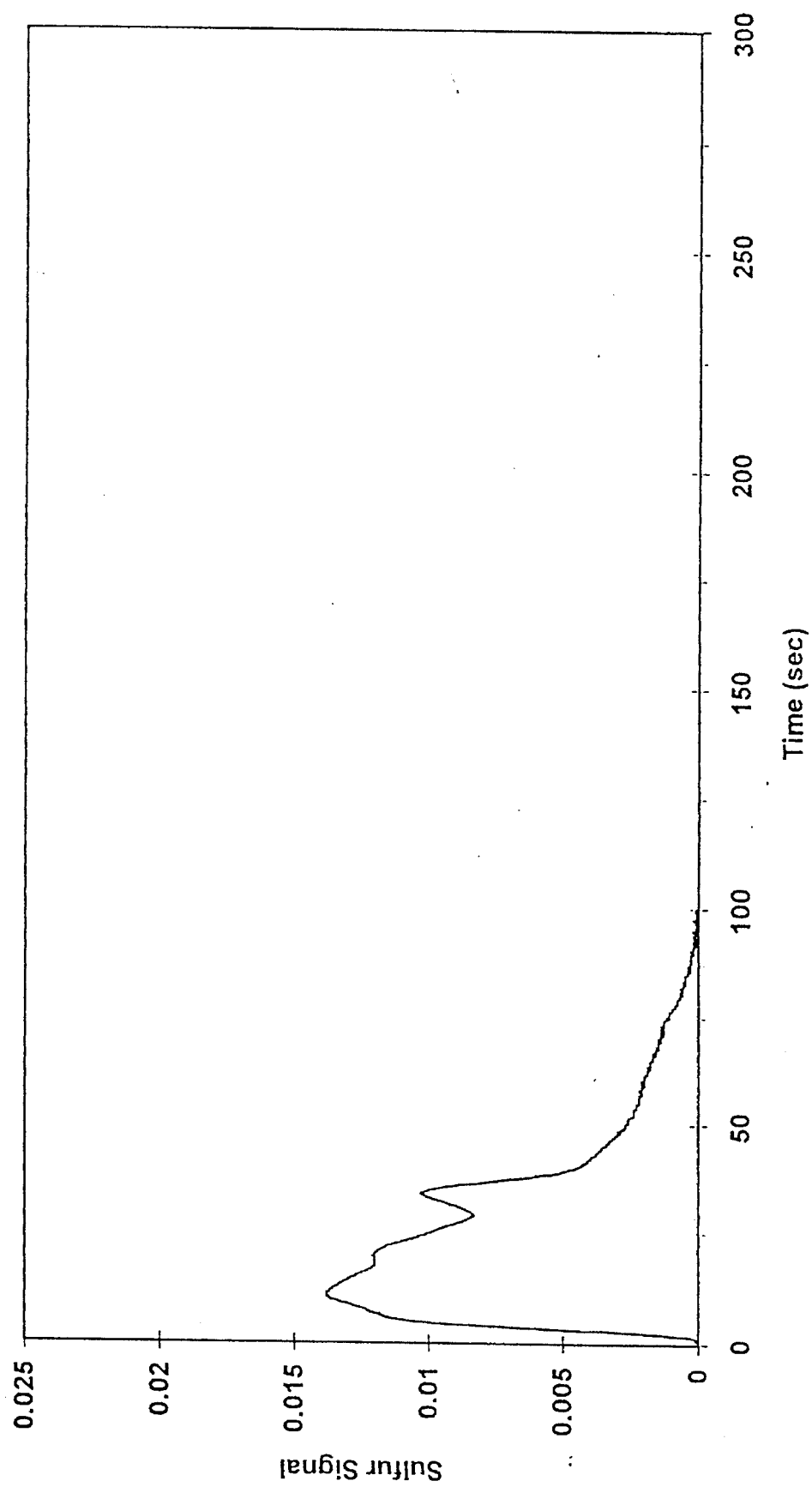
FIG. 25 shows the sulfur signal as a function of time for tobacco with a mixture of compound comprising tungsten oxide ($WO_3$) and lithium metaphosphate ($LiPO_3$) with 20:1 weight ratio as the accelerator tested at 1350° C.

Five grams of tungsten oxide ($WO_3$) and 0.25 grams of the same lithium metaphosphate ($LiPO_3$) used in example 2 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1350° C. for sulfur determination. All of the sulfur signal came off within approximately 90 seconds. FIG. 25 shows the result of the sulfur signal as a function of analysis time.

Figure 26:
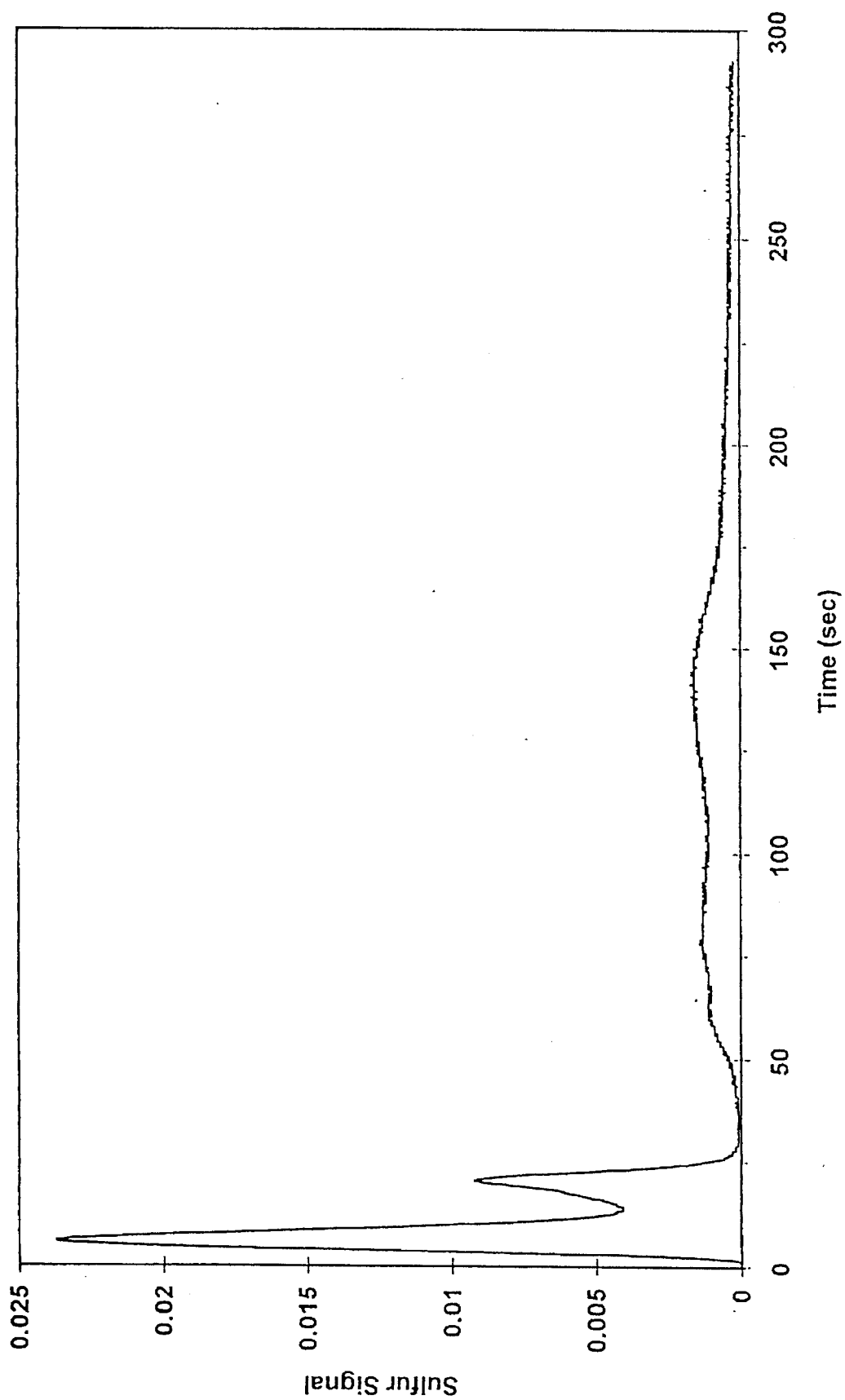
FIG. 26 shows the sulfur signal as a function of time for tobacco without any accelerator tested at 1350° C.

Example 26 - Comparative 0.15 grams of Tobacco was weighed into a ceramic boat. The ceramic boat with Tobacco was pushed into the combustion tube of the SC-444 at 1350° C. for sulfur determination. The sulfur signal extends to approximately 300 seconds. Also, the total amount of sulfur released was reduced to approximately 80% compared to that of example 11. FIG. 26 shows the result of the sulfur signal as a function of analysis time.

Example 27

Figure 27:
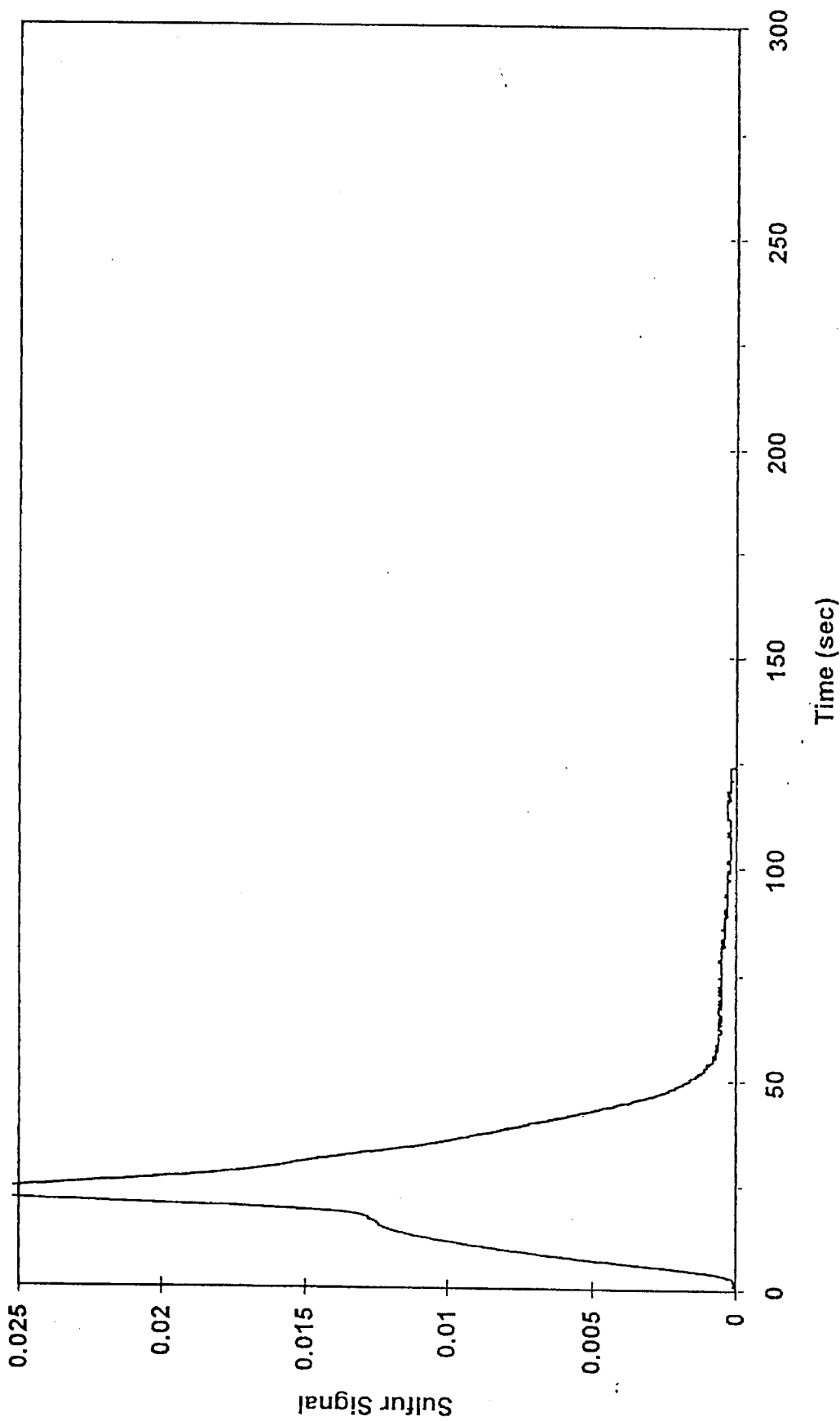
FIG. 27 shows the sulfur signal as a function of time for tobacco with lithium metaphosphate ($LiPO_3$) as the accelerator tested at 1250° C.

Two grams of the same lithium metaphosphate (LiPO$_3$) used in example 2 was weighed into a ceramic boat followed by 0.15 grams of Tobacco. Tobacco and lithium metaphosphate were blended by hand using a spatula. The ceramic boat with blended Tobacco and lithium metaphosphate was pushed into the combustion tube of the SC-444 at 1250° C. for sulfur determination. All of the sulfur signal came off within approximately 125 seconds. FIG. 27 shows the result of the sulfur signal as a function of analysis time.

Example 28

Figure 28:
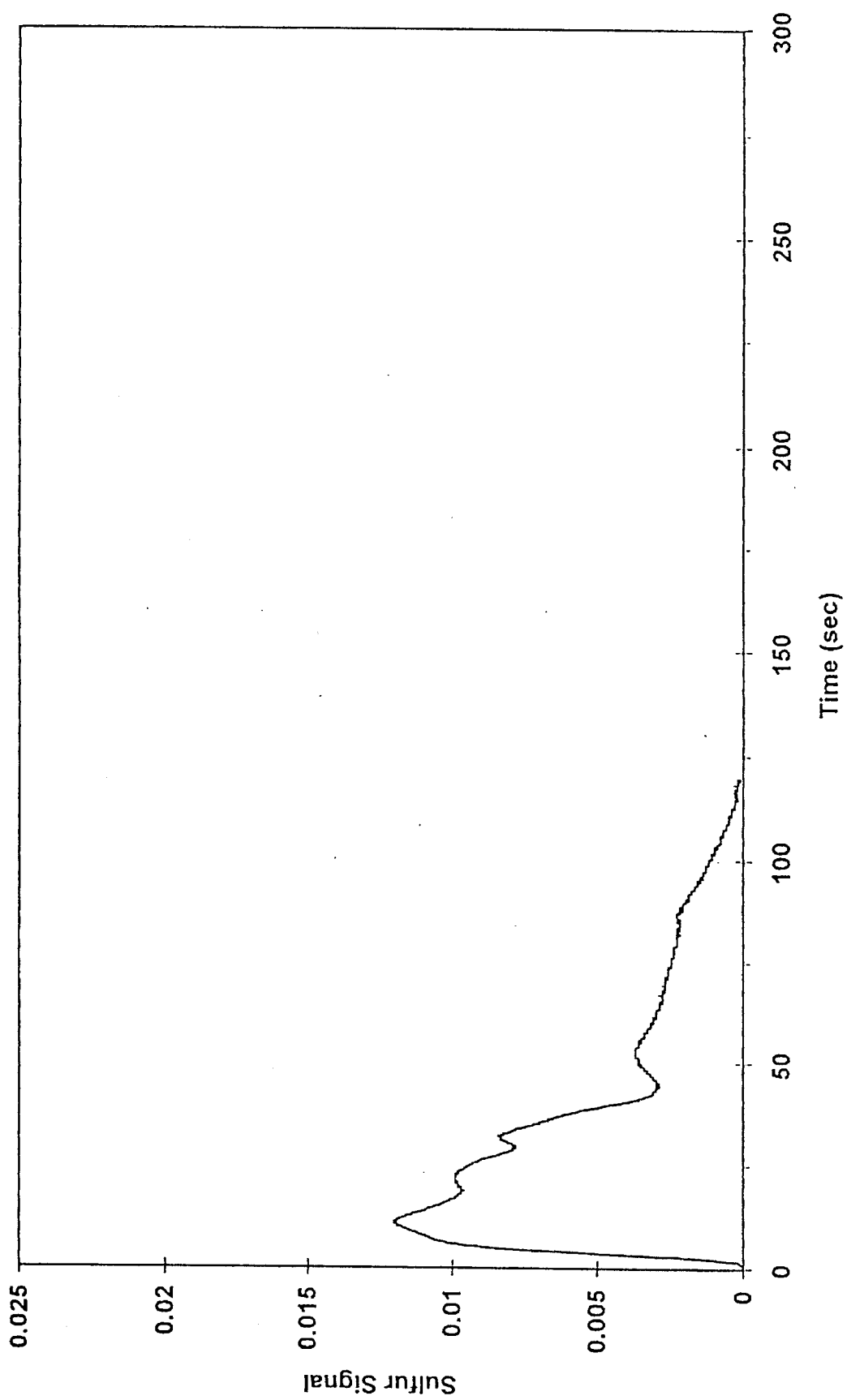
FIG. 28 shows the sulfur signal as a function of time for tobacco with a mixture of compound comprising tungsten oxide ($WO_3$) and lithium metaphosphate ($LiPO_3$) with 20:1 weight ratio as the accelerator tested at 1250° C.

Five grams of tungsten oxide (WO$_3$) and 0.25 grams of the same lithium metaphosphate (LiPO$_3$) used in example 2 were uniformly dry mixed in a mortar and pestal. The mixture was added in a ceramic boat followed by 0.15 grams of Tobacco. Tobacco and the mixture were blended by hand using a spatula. The ceramic boat with blended Tobacco and mixture was pushed into the combustion tube of the SC-444 at 1250° C. for sulfur determination. All of the sulfur signal came off within approximately 120 seconds. FIG. 28 shows the result of the sulfur signal as a function of analysis time.

Figure 29:
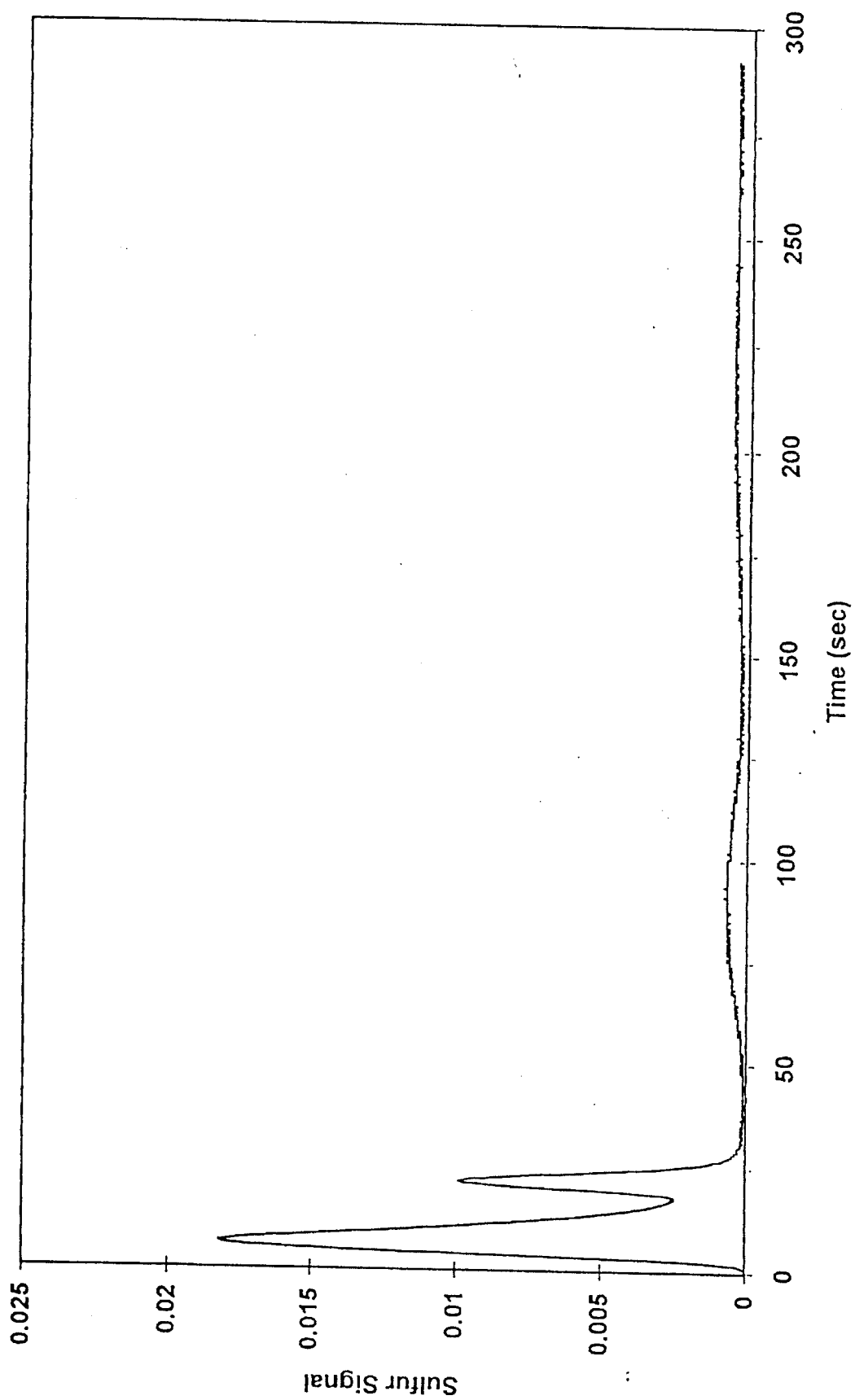
FIG. 29 shows the sulfur signal as a function of time for tobacco without any accelerator tested at 1250° C.

Example 29 - Comparative 0.15 grams of Tobacco was weighed in the ceramic boat. The ceramic boat with Tobacco was pushed into the combustion tube of the SC-444 at 1250° C. for sulfur determination. The sulfur signal extends to approximately 300 seconds. Also, the total amount of sulfur released was reduced to approximately 60% compared to that of example 11. FIG. 29 shows the result of the sulfur signal as a function of analysis time.

The above description is considered that of the preferred embodiment only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

The embodiments of the invention in which an exclusive property or privilege is claimed are defined as follows:

1. A method for conducting an elemental analysis of a substance comprising mixing said substance with a non-toxic accelerator for accelerating the combustion of said substance, said non-toxic accelerator comprising a compound selected from the group consisting of glass frit, niobium pentoxide, inorganic phosphates and mixtures thereof;

heating the resulting mixture to at least the decomposition temperature of said substance to be analyzed; and analyzing the products of decomposition for the element to be analyzed for.

2. The method of claim 1 wherein the non-toxic accelerator has a particle size of less than about 2 mm.

3. The method of claim 1 wherein the non-toxic accelerator has a particle size of from about 0.1 to about 20 µm.

4. The method of claim 1 wherein the inorganic phosphate is lithium metaphosphate.

5. The method of claim 1 wherein the inorganic phosphate is potassium dihydrogen phosphate.

6. The method of claim 1 in which tungsten oxide is also added to said non-toxic accelerator.

7. A method for conducting an elemental analysis of a substance comprising mixing said substance with a non-toxic accelerator for accelerating the combustion of said substance, said non-toxic accelerator comprising glass frit;

heating the resulting mixture to at least the decomposition temperature of said substance to be analyzed; and analyzing the products of decomposition for the element to be analyzed for.

8. The method of claim 7 wherein the non-toxic accelerator has a particle size of less than about 2 mm.

9. The method of claim 7 wherein the non-toxic accelerator has a particle size of from about 0.1 to about 20 µm.

10. A method for conducting an elemental analysis of a substance comprising mixing said substance with a non-toxic accelerator for accelerating the combustion of said substance, said non-toxic accelerator comprising niobium pentoxide;

heating the resulting mixture to at least the decomposition temperature of said substance to be analyzed; and analyzing the products of decomposition for the element to be analyzed for.

11. The method of claim 10 wherein the non-toxic accelerator has a particle size of less than about 2 mm.

12. The method of claim 10 wherein the non-toxic accelerator has a particle size of from about 0.1 to about 20 µm.

13. A method for conducting an elemental analysis of a substance comprising mixing said substance with a non-toxic accelerator for accelerating the combustion of said substance, said non-toxic accelerator comprising inorganic phosphates;

heating the resulting mixture to at least the decomposition temperature of said substance to be analyzed; and analyzing the products of decomposition for the element to be analyzed for.

14. The method of claim 13 wherein the non-toxic accelerator has a particle size of less than about 2 mm.

15. The method of claim 13 wherein the non-toxic accelerator has a particle size of from about 0.1 to about 20 µm.

16. The method of claim 13 wherein the inorganic phosphate is lithium metaphosphate.

17. The method of claim 13 wherein the inorganic phosphate is potassium dihydrogen phosphate.

18. A method for conducting an elemental analysis of a substance comprising mixing said substance with a non-toxic accelerator for accelerating the combustion of said substance, said non-toxic accelerator comprising a mixture of (a) a component selected from the group consisting of tungsten oxide, niobium pentoxide and mixtures thereof, and (b) a component selected from the group consisting of glass frit, inorganic phosphates and mixtures thereof;

heating the resulting mixture to at least the decomposition temperature of said substance to be analyzed; and analyzing the products of decomposition for the element to be analyzed for.

19. The method of claim 18 wherein the non-toxic accelerator has a particle size of less than about 2 mm.

20. The method of claim 18 wherein the non-toxic accelerator has a particle size of from about 0.1 to about 20 µm.

21. The method of claim 18 wherein the inorganic phosphate is lithium metaphosphate.

22. The method of claim 18 wherein the inorganic phosphate is potassium dihydrogen phosphate.

23. The method of claim 18 wherein the non-toxic accelerator has a weight ratio of component (a) to component (b) of from about 40:1 to about 10:1.

24. The method of claim 18 wherein the non-toxic accelerator has a weight ratio of component (a) to component (b) of about 20:1.

25. The method of claim 18 wherein all components are combined by dry mixing.

26. The method of claim 25 wherein the dry mixing is followed by melt-mixing at a temperature of from about 300° C. to about 1700° C., followed by grinding into a powder.

27. The method of claim 18 wherein all components are combined by wet mixing in a water solution, followed by drying and grinding into a powder.

28. The method of claim 27 wherein the wet-mixing in a water solution is followed by heat treating at a temperature of from about 300° C. to about 1700° C. followed by grinding into a powder.

29. The method of claim 18 wherein all components are combined by wet mixing in a solvent solution, followed by drying and grinding into a powder.

30. The method of claim 29 wherein the wet mixing in a solvent solution is followed by heat treating at a temperature of from about 300° C. to about 1700° C. followed by grinding into a powder.

31. A powdered non-toxic combustion accelerator for elemental analysis comprising a powder mixture of (a) a component selected from the group consisting of tungsten oxide, niobium pentoxide and mixtures thereof, and (b) a component selected from the group consisting of glass frit, inorganic phosphates and mixtures thereof, wherein the non-toxic accelerator has a weight ratio of component (a) to component (b) of from about 40:1 to about 10:1.

32. A powdered non-toxic combustion accelerator for elemental analysis comprising a powder mixture of (a) a component selected from the group consisting of tungsten oxide, niobium pentoxide and mixtures thereof, and (b) a component selected from the group consisting of glass frit, inorganic phosphates and mixtures thereof, wherein the non-toxic accelerator has a weight ratio of component (a) to component (b) of about 20:1.

33. A powdered non-toxic combustion accelerator for elemental analysis comprising a powder mixture of (a) a component selected from the group consisting of tungsten oxide, niobium pentoxide and mixtures thereof, and (b) a component selected from the group consisting of glass frit, inorganic phosphates and mixtures thereof, wherein all components are combined by dry mixing, followed by melt-mixing at a temperature of from about 500° C. to about 700° C., followed by grinding into a powder.

34. A powdered non-toxic combustion accelerator for elemental analysis comprising a powder mixture of (a) a component selected from the group consisting of tungsten oxide, niobium pentoxide and mixtures thereof, and (b) a component selected from the group consisting of glass frit, inorganic phosphates and mixtures thereof, wherein all components are combined by wet mixing in a water solution, followed by heat treating at a temperature of from about 500° C. to about 700° C., followed by grinding into a powder.

35. A powdered non-toxic combustion accelerator for elemental analysis comprising a powder mixture of (a) a component selected from the group consisting of tungsten oxide, niobium pentoxide and mixtures thereof, and (b) a component selected from the group consisting of glass frit, inorganic phosphates and mixtures thereof, wherein all components are combined by wet mixing in a solvent solution, followed by heat treating at a temperature of from about 500° C. to about 700° C., followed by grinding into a powder.

36. A method for making a non-toxic combustion accelerator which comprises combining (a) a component selected from the group consisting of tungsten oxide, niobium pentoxide and mixtures thereof, and (b) a component selected from the group consisting of glass frit, inorganic phosphates and mixtures thereof, wherein all components are combined by dry mixing, followed by melt-mixing at a temperature of from about 500° C. to about 700° C., followed by grinding into a powder.

37. A method of making a non-toxic combustion accelerator which comprises combining (a) a component selected from the group consisting of tungsten oxide, niobium pentoxide and mixtures thereof, and (b) a component selected from the group consisting of glass frit, inorganic phosphates and mixtures thereof, wherein all components are combined by wet mixing in a water solution, followed by heat treating at a temperature of from about 500° C. to about 700° C., followed by grinding into a powder.

38. A method of making a non-toxic combustion accelerator which comprises combining (a) a component selected from the group consisting of tungsten oxide, niobium pentoxide and mixtures thereof, and (b) a component selected from the group consisting of glass frit, inorganic phosphates and mixtures thereof, wherein all components are combined by wet mixing in a solvent solution, followed by heat treating at temperature of from about 500° C. to about 700° C., followed by grinding into a powder.

* * * * *

UNITED STATES PATENT AND TRADEMARK OFFICE
CERTIFICATE OF CORRECTION

PATENT NO. : 5,547,876
DATED : August 20, 1996
INVENTOR(S) : Chen et al.

It is certified that error appears in the above-identified patent and that said Letters Patent is hereby corrected as shown below:

Col. 6, line 62, "tobacco" should be --Tobacco--;

Col. 9, line 27, insert a blank line before and after and center "Example 18";

Col. 9, line 32, "tobacco" should be --Tobacco--;

Col. 10, line 33, "450°C" should be --1450°C--; and

Col. 11, line 50, "doctrine of equivalents" should be --Doctrine of Equivalents--.

Signed and Sealed this

Eleventh Day of February, 1997

Attest:

BRUCE LEHMAN

*Attesting Officer*     *Commissioner of Patents and Trademarks*